(12) United States Patent
Scates et al.

(10) Patent No.: US 8,592,635 B2
(45) Date of Patent: Nov. 26, 2013

(54) INTEGRATED ETHANOL PRODUCTION BY EXTRACTING HALIDES FROM ACETIC ACID

(75) Inventors: Mark O. Scates, Houston, TX (US); Ronald D. Shaver, Houston, TX (US); James H. Zink, League City, TX (US); Raymond J. Zinobile, Houston, TX (US); Oyeyemi Oyerinde, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 197 days.

(21) Appl. No.: 13/292,899

(22) Filed: Nov. 9, 2011

(65) Prior Publication Data

US 2012/0277489 A1    Nov. 1, 2012

(51) Int. Cl.
*C07C 29/149* (2006.01)
(52) U.S. Cl.
USPC ........................................................ 568/885
(58) Field of Classification Search
USPC ........................................................ 568/885
See application file for complete search history.

(56) References Cited

U.S. PATENT DOCUMENTS

| | | |
|---|---|---|
| 1,939,116 A | 12/1933 | Fuchs |
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,709,795 A | 1/1973 | Singleton |
| 3,769,329 A | 10/1973 | Paulik et al. |
| 3,864,284 A | 2/1975 | Clippinger et al. |
| 3,884,981 A | 5/1975 | Kiff |
| 3,925,490 A | 12/1975 | Reich et al. |
| 3,990,952 A | 11/1976 | Katzen et al. |
| 4,008,131 A | 2/1977 | Price |
| 4,039,395 A | 8/1977 | Eby |
| 4,107,002 A | 8/1978 | Eck et al. |
| 4,126,539 A | 11/1978 | Derr, Jr. et al. |
| 4,149,940 A | 4/1979 | Pinto |
| 4,262,154 A | 4/1981 | Gane et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,328,375 A | 5/1982 | Barlow |
| 4,338,221 A | 7/1982 | Qualeatti |
| 4,352,940 A | 10/1982 | Adelman et al. |
| 4,352,947 A | 10/1982 | Habib et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa et al. |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,451,677 A | 5/1984 | Bradley et al. |
| 4,454,358 A | 6/1984 | Kummer et al. |
| 4,456,775 A | 6/1984 | Travers et al. |
| 4,465,854 A | 8/1984 | Pond et al. |
| 4,471,136 A | 9/1984 | Larkins et al. |
| 4,476,326 A | 10/1984 | Lin et al. |
| 4,480,115 A | 10/1984 | McGinnis |
| 4,481,146 A | 11/1984 | Leupold et al. |
| 4,492,808 A | 1/1985 | Hagen et al. |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster, Ludwig et al. |
| 4,520,213 A | 5/1985 | Victor |
| 4,541,897 A | 9/1985 | Sommer et al. |
| 4,556,644 A | 12/1985 | Erpenbach et al. |
| 4,569,726 A | 2/1986 | Berg et al. |
| 4,611,085 A | 9/1986 | Kitson |
| 4,626,321 A | 12/1986 | Grethlein et al. |
| 4,626,604 A | 12/1986 | Hiles et al. |

(Continued)

FOREIGN PATENT DOCUMENTS

| CA | 1233484 | 3/1988 |
|---|---|---|
| CN | 1230458 | 10/1999 |

(Continued)

OTHER PUBLICATIONS

Zheng, et al. (2007). Preparation and calatyltic properties of a bimetallic Sn-Pt complex in the supercages of NaY zeolite by use of surface organometallic chemistry, Applied Organometallic Chemistry, 21(10), 836-840.

(Continued)

*Primary Examiner* — Elvis O Price

(57) ABSTRACT

This invention relates to a process for producing ethanol and recovering methyl iodide, the process comprising the steps of carbonylating methanol in a carbonylation system in the presence of a carbonylation catalyst under conditions effective to form acetic acid; hydrogenating the acetic acid in a hydrogenation system in the presence of a hydrogenation catalyst to form a crude ethanol product comprising ethanol and water; and separating the crude ethanol product to form an ethanol stream and a water stream.

22 Claims, 6 Drawing Sheets

(56) References Cited

U.S. PATENT DOCUMENTS

| | | |
|---|---|---|
| 4,628,130 A | 12/1986 | Bournonville et al. |
| 4,629,711 A | 12/1986 | Erpenbach et al. |
| 4,664,753 A | 5/1987 | Erpenbach et al. |
| 4,678,543 A | 7/1987 | Houben et al. |
| 4,692,218 A | 9/1987 | Houben et al. |
| 4,737,318 A | 4/1988 | Ichino et al. |
| 4,751,334 A | 6/1988 | Turner et al. |
| 4,758,600 A | 7/1988 | Arimitsu et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,837,367 A | 6/1989 | Gustafson et al. |
| 4,837,368 A | 6/1989 | Gustafson et al. |
| 4,842,693 A | 6/1989 | Wheldon |
| 4,876,402 A | 10/1989 | Logsdon et al. |
| 4,886,905 A | 12/1989 | Larkins, Jr. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,992,582 A | 2/1991 | Ruppert et al. |
| 4,994,608 A | 2/1991 | Torrence et al. |
| 5,001,259 A | 3/1991 | Smith et al. |
| 5,004,845 A | 4/1991 | Bradley et al. |
| 5,026,908 A | 6/1991 | Smith et al. |
| 5,035,776 A | 7/1991 | Knapp |
| 5,047,592 A | 9/1991 | Carpenter |
| 5,061,671 A | 10/1991 | Kitson et al. |
| 5,070,016 A | 12/1991 | Hallberg |
| 5,124,004 A | 6/1992 | Grethlein et al. |
| 5,144,068 A | 9/1992 | Smith et al. |
| 5,149,680 A | 9/1992 | Kitson et al. |
| 5,185,476 A | 2/1993 | Gustafson |
| 5,185,481 A | 2/1993 | Muto et al. |
| 5,196,601 A | 3/1993 | Kitsuki et al. |
| 5,198,592 A | 3/1993 | van Beijnum et al. |
| 5,215,902 A | 6/1993 | Tedder |
| 5,220,020 A | 6/1993 | Buchwald et al. |
| 5,227,141 A | 7/1993 | Kim et al. |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe et al. |
| 5,254,758 A | 10/1993 | Hiles et al. |
| 5,284,983 A | 2/1994 | Muto et al. |
| 5,300,685 A | 4/1994 | Scates et al. |
| 5,334,751 A | 8/1994 | Lemanski et al. |
| 5,348,625 A | 9/1994 | Berg |
| 5,362,918 A | 11/1994 | Aizawa et al. |
| 5,399,752 A | 3/1995 | Okrasinski et al. |
| 5,403,962 A | 4/1995 | Schneider et al. |
| 5,414,161 A | 5/1995 | Uhm et al. |
| 5,415,741 A | 5/1995 | Berg |
| 5,416,237 A | 5/1995 | Aubigne et al. |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,476,974 A | 12/1995 | Moore et al. |
| 5,480,665 A | 1/1996 | Smith |
| 5,502,094 A | 3/1996 | Moore et al. |
| 5,502,248 A | 3/1996 | Funk et al. |
| 5,527,969 A | 6/1996 | Kaufhold et al. |
| 5,567,765 A | 10/1996 | Moore et al. |
| RE35,377 E | 11/1996 | Steinberg et al. |
| 5,599,976 A | 2/1997 | Scates et al. |
| 5,658,962 A | 8/1997 | Moore et al. |
| 5,696,284 A | 12/1997 | Baker et al. |
| 5,731,252 A | 3/1998 | Warner et al. |
| 5,747,486 A | 5/1998 | Sohda et al. |
| 5,762,765 A | 6/1998 | Berg |
| 5,770,761 A | 6/1998 | Lin et al. |
| 5,770,770 A | 6/1998 | Kim et al. |
| 5,800,681 A | 9/1998 | Berg |
| 5,821,111 A | 10/1998 | Gaddy et al. |
| 5,831,133 A | 11/1998 | Mimoun |
| 5,861,530 A | 1/1999 | Atkins et al. |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,973,193 A | 10/1999 | Crane et al. |
| 5,993,610 A | 11/1999 | Berg |
| 5,998,658 A | 12/1999 | Wu et al. |
| 6,024,176 A | 2/2000 | Moore et al. |
| 6,040,474 A | 3/2000 | Jobson et al. |
| 6,046,127 A | 4/2000 | Mimoun |
| 6,093,845 A | 7/2000 | Van Acker et al. |
| 6,121,497 A | 9/2000 | Murphy |
| 6,140,535 A | 10/2000 | Williams |
| 6,143,930 A | 11/2000 | Singh et al. |
| 6,204,299 B1 | 3/2001 | Moore et al. |
| 6,214,253 B1 | 4/2001 | Moore et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,458,996 B1 | 10/2002 | Muskett |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,555 B2 | 10/2002 | Choudary et al. |
| 6,486,366 B1 | 11/2002 | Ostgard et al. |
| 6,491,983 B2 | 12/2002 | Moore et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,525,230 B2 | 2/2003 | Grosso |
| 6,552,220 B1 | 4/2003 | Obana et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,713,655 B2 | 3/2004 | Yilmaz et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,863,211 B2 | 3/2005 | Moore et al. |
| 6,867,164 B2 | 3/2005 | Obana et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,019,182 B2 | 3/2006 | Grosso |
| 7,074,603 B2 | 7/2006 | Verser et al. |
| 7,084,312 B1 | 8/2006 | Huber et al. |
| 7,091,155 B2 | 8/2006 | Inui et al. |
| 7,115,772 B2 | 10/2006 | Picard et al. |
| 7,148,390 B2 | 12/2006 | Zhou et al. |
| 7,161,050 B2 | 1/2007 | Sherman et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,230,150 B2 | 6/2007 | Grosso et al. |
| 7,297,236 B1 | 11/2007 | Vander Griend et al. |
| 7,351,559 B2 | 4/2008 | Verser et al. |
| 7,361,794 B2 | 4/2008 | Grosso |
| 7,375,049 B2 | 5/2008 | Hayes et al. |
| 7,399,892 B2 | 7/2008 | Rix et al. |
| 7,507,562 B2 | 3/2009 | Verser et al. |
| 7,538,060 B2 | 5/2009 | Barnicki et al. |
| 7,553,397 B1 | 6/2009 | Colley et al. |

(56) References Cited

U.S. PATENT DOCUMENTS

| | | |
|---|---|---|
| 7,572,353 B1 | 8/2009 | Vander et al. |
| 7,601,865 B2 | 10/2009 | Verser et al. |
| 7,608,744 B1 | 10/2009 | Johnston et al. |
| 7,652,167 B2 | 1/2010 | Miller et al. |
| 7,667,068 B2 | 2/2010 | Miller et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,820,852 B2 | 10/2010 | Johnston et al. |
| 7,834,223 B2 | 11/2010 | Atkins et al. |
| 7,838,708 B2 | 11/2010 | Sherman et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 7,964,379 B2 | 6/2011 | Verser et al. |
| 7,994,368 B2 | 8/2011 | Johnston et al. |
| 8,071,821 B2 | 12/2011 | Johnston et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0013908 A1 | 1/2003 | Horan et al. |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0114719 A1 | 6/2003 | Fischer et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0009614 A1 | 1/2004 | Ahn et al. |
| 2004/0063184 A1 | 4/2004 | Grichko |
| 2004/0152915 A1 | 8/2004 | Fujita et al. |
| 2004/0232049 A1 | 11/2004 | Dath et al. |
| 2004/0242917 A1 | 12/2004 | Inui et al. |
| 2004/0267074 A1 | 12/2004 | Grosso et al. |
| 2005/0043572 A1 | 2/2005 | Grosso |
| 2005/0192468 A1 | 9/2005 | Sherman et al. |
| 2005/0197506 A1 | 9/2005 | Scates et al. |
| 2005/0209328 A1 | 9/2005 | Allgood et al. |
| 2005/0214408 A1 | 9/2005 | Pilkington et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2006/0224013 A1 | 10/2006 | Inui et al. |
| 2006/0247466 A1 | 11/2006 | Zinobile et al. |
| 2006/0252956 A1 | 11/2006 | Miller et al. |
| 2007/0031954 A1 | 2/2007 | Mairal et al. |
| 2007/0265360 A1 | 11/2007 | Luo et al. |
| 2007/0270511 A1 | 11/2007 | Melnichuk et al. |
| 2008/0103335 A1 | 5/2008 | Scates et al. |
| 2008/0135396 A1 | 6/2008 | Blum |
| 2008/0187472 A1 | 8/2008 | Ahn et al. |
| 2008/0193989 A1 | 8/2008 | Verser et al. |
| 2008/0207953 A1 | 8/2008 | Houssin et al. |
| 2008/0257784 A1 | 10/2008 | Dath et al. |
| 2008/0269518 A1 | 10/2008 | Scates et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0099389 A1 | 4/2009 | Shaver |
| 2009/0166172 A1 | 7/2009 | Casey |
| 2009/0221725 A1 | 9/2009 | Chornet et al. |
| 2009/0264285 A1 | 10/2009 | Luo et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2009/0326268 A1 | 12/2009 | Hanes et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0041919 A1 | 2/2010 | Wu et al. |
| 2010/0063319 A1 | 3/2010 | Brtko et al. |
| 2010/0069515 A1 | 3/2010 | Tirtowidjojo et al. |
| 2010/0080736 A1 | 4/2010 | Hassan et al. |
| 2010/0121114 A1 | 5/2010 | Johnston et al. |
| 2010/0121119 A1 | 5/2010 | Sherman et al. |
| 2010/0137630 A1 | 6/2010 | Garton et al. |
| 2010/0145097 A1 | 6/2010 | Brtko et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2010/0249479 A1 | 9/2010 | Berg-Slot et al. |
| 2010/0261800 A1 | 10/2010 | Daniel et al. |
| 2010/0273229 A1 | 10/2010 | Verser et al. |
| 2010/0311138 A1 | 12/2010 | Padgett |
| 2011/0004033 A1 | 1/2011 | Johnston et al. |
| 2011/0004034 A1 | 1/2011 | Daniel et al. |
| 2011/0034741 A1 | 2/2011 | Sherman et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0190547 A1 | 8/2011 | Jevtic et al. |
| 2011/0190548 A1 | 8/2011 | Jevtic et al. |
| 2011/0190552 A1 | 8/2011 | Powell et al. |
| 2011/0224462 A1 | 9/2011 | Ditzel et al. |
| 2011/0263911 A1 | 10/2011 | Johnston et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| CN | 1944373 | 4/2007 |
| CN | 1944374 | 4/2007 |
| CN | 101665424 | 3/2010 |
| CN | 201768393 | 3/2011 |
| CN | 102228831 | 11/2011 |
| CN | 102229520 | 11/2011 |
| DE | 241590 | 12/1986 |
| DE | 60025239 | 6/2006 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0535825 | 5/1996 |
| EP | 0944572 | 9/1999 |
| EP | 0990638 | 4/2000 |
| EP | 0992482 | 4/2000 |
| EP | 1338587 | 8/2003 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |

(56) References Cited

FOREIGN PATENT DOCUMENTS

| | | |
|---|---|---|
| EP | 2186787 | 5/2010 |
| JP | 60-09454 | 1/1985 |
| JP | 60-25033 | 2/1985 |
| JP | 61-28181 | 2/1986 |
| JP | 02-215790 | 8/1990 |
| JP | 51-86391 | 7/1993 |
| JP | 6-116182 | 4/1994 |
| JP | 2001-046874 | 2/2001 |
| JP | 2001-157841 | 6/2001 |
| JP | 2005-289936 | 10/2005 |
| KR | 2012-0010763 | 2/2012 |
| WO | WO 82/03854 | 11/1982 |
| WO | WO 83/03409 | 10/1983 |
| WO | WO 98/25876 | 6/1998 |
| WO | WO 2002/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/103948 | 8/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/030320 | 3/2010 |
| WO | WO 2010/055285 | 5/2010 |
| WO | WO 2011/053365 | 5/2011 |
| WO | WO 2011/056597 | 5/2011 |
| WO | WO 2011/097193 | 8/2011 |
| WO | WO 2011/097208 | 8/2011 |
| WO | WO 2011/097217 | 8/2011 |
| WO | WO 2011/097219 | 8/2011 |
| WO | WO 2011/097220 | 8/2011 |
| WO | WO 2011/140455 | 11/2011 |
| WO | WO 2011/140485 | 11/2011 |
| WO | WO 2012/006228 | 1/2012 |
| WO | WO 2012/006388 | 1/2012 |
| WO | WO 2012/006499 | 1/2012 |

OTHER PUBLICATIONS

ZeaChem, Inc., Technology Overview, Lakewood, Colorado www.zeachem.com, 2008.

Santori et al.(2000). Hydrogenation of carbonylic compounds on Pt/SiO2 catalysis modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Witzeman and Agreda, "Safety and Performance Assessment of Ethanol/Diesel Blends (e-blend)" NREL/SR-540-34817, at p. 1-1, Sep. 2003.

Michael Gauβ, et al., Applied Homogeneous Catalysis with Organometallic Compounds: A Comprehensive Handbook in two Volume, Chapter 2.1, p. 27-200, (1st ed., 1996).

Juran et al., "Convert Methanol to Ethanol", Hydrocarbon Processing, Oct. 1985, pp. 85-87.

Zhang et al., Hydrogenation of Ethyl Acetate to Ethanol over Ni-Based Catalysts Obtained from Ni/Ai Hydrotalcite-Like Compounds. Molecules 2010, 15, 5139-5152, 2010.

Claus, et al., "Selective Hydrogenolysis of methyl and ethyl acetate in the gas phase on copper and supported Group VIII metal catalysts", Applied Catalysis A, 79, 1991, p. 1-18.

Y. Zhu et al., "Techno-economic Analysis for the Thermochemical Conversion of Lignocellulosic Biomass to Ethanol via Acetic Acid Synthesis", Apr. 1, 2009, pp. 1-71 (80 Pages).

Pestman et al., Identification of the Active Sites in the Selective Hydrogenation of Acetic Acid to Acetaldehyde on Iron Oxide Catalysts, Journal of Catalysis 174:142-152 (1998).

Kita H., et al., "Synthesis of a Zeolite Naa Membrane for Pervaporation of Water/Organic Liquid Mixtures", Journal of Materials Science Letters, vol. 14, Jan. 1, 1995, pp. 206-208.

Calvar, et al., "Esterification of acetic acid and ethanol: Reaction kinetics and operation in a packed bed reactive distillation column", Chem Engineering and Processing, vol. 46, No. 12, Oct. 9, 2007, pp. 1317-1323.

Marian Simo, et al., "Adsorption/Desorption of Water and Ethanol on 3A Zeolite in Neo-Adiabatic Fixed Bed", Industrial and Engineering Chemistry Research, vol. 48, No. 20, Sep. 25, 2009, pp. 9247-9260.

Benson, Tracy J., et al., "Cellulose Based Adsorbent Materials for the Dehydration of Ethanol Using Thermal Swing Adsorption", Adsorption, Kluwer Academic Publishers, vol. 11, No. 1, Jul. 1, 2005, pp. 697-701.

Yu Huang, et al., "Low-Energy Distillation-Membrane separation Process", Industrial & Engineering Chemistry Research, Am. Chem. Soc., vol. 49, No. 8, Jan. 1, 2010, pp. 3760-3768.

H. Constantin et al., "Influence of C-Sources on the Denitrification Rate of a High-Nitrate Concentrated Industrial Wastewater", Wat. Res. vol. 31, No. 3, 1997, pp. 583-589.

Anonymous: "Studies in Extractive and Azeotropic Distillation Series; Study No. 4—Separation of Alcohols from the Acetate/Alcohol/Water Ternary by Extractive Distillation" May 9, 2008, pp. 1-9.

V. Ragaini et al., "Increasing the value of dilute acetic acid streams through esterification Part 1. Experimental analysis of the reaction zone", Applied Catalysis B: Environmental, vol. 64, 2006, pp. 66-71.

International Search Report and Written Opinion for PCT/US2011/060020 mailed Sep. 11, 2012.

International Search Report and Written Opinion for PCT/US2011/059891 mailed Jul. 30, 2012.

International Search Report and Written Opinion for PCT/US2012/035273 mailed Jul. 30, 2012.

International Preliminary Report on Patentability mailed Jun. 27, 2012 in corresponding International Application No. PCT/US2011/023276.

International Search Report and Written Opinion for PCT/US2011/023276 mailed Sep. 2, 2011.

International Search Report and Written Opinion mailed on Aug. 11, 2011 in corresponding International Application No. PCT/US2011/023283.

Written Opinion mailed on Jan. 30, 2012 in corresponding International Application No. PCT/US2011/023283.

International Search Report and Written Opinion mailed Sep. 6, 2011 in corresponding International Application No. PCT/US2011/023338.

Invitation to Pay Additional Fees and Partial Search Report mailed May 4, 2011 in corresponding International Application No. PCT/US2011/023283.

International Preliminary Report on Patentability mailed May 18, 2012 in corresponding International Application No. PCT/US2011/023283.

Written Opinion mailed May 16, 2012 in corresponding International Application No. PCT/US2011/023338.

International Preliminary Report on Patentability mailed Jul. 5, 2012 in corresponding International Application No. PCT/US2011/023338.

International Search Report and Written Opinion mailed May 31, 2012 in corresponding International Application No. PCT/US2011/043213.

(56) References Cited

OTHER PUBLICATIONS

International Search Report and Written Opinion mailed Jun. 11, 2012 in corresponding International Application No. PCT/US2012/020977.

Invitation to Pay Fees mailed Mar. 13, 2012 in corresponding International Application No. PCT/US2012/020977.

International Search Report and Written Opinion mailed Mar. 14, 2012 in corresponding International Application No. PCT/US2012/020979.

International Search Report and Written Opinion for PCT/US2011/043310 dated Feb. 23, 2012.

International Search Report and Written Opinion mailed Jul. 12, 2012 in corresponding International Application No. PCT/US2012/035166.

International Search Report and Written Opinion mailed Jul. 6, 2012 in corresponding International Application No. PCT/US2011/059889.

International Search Report and Written Opinion for PCT/US2011/060019 mailed Apr. 19, 2012.

International Search Report and Written Opinion for PCT/US2012/035189 mailed Jul. 30, 2012.

International Search Report and Written Opinion for PCT/US2011/060014 mailed Jun. 29, 2012.

International Search Report and Written Opinion for PCT/US2012/035220 mailed Aug. 2, 2012.

International Search Report and Written Opinion for PCT/US2012/035196 mailed Aug. 6, 2012.

International Search Report and Written Opinion for PCT/US2012/035203 mailed Jul. 11, 2012.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

J. Jones, et al., Platinum Metals Review, vol. 44, No. 3, pp. 94-104 (Jul. 2000).

Acala, et al., (2005). Experimental and DFT studies of the conversion of ethanol and acetic acid on PtSn-based catalysts, Journal of Physical Chemistry, 109(6), 2074-2085.

INTEGRATED ETHANOL PRODUCTION BY EXTRACTING HALIDES FROM ACETIC ACID

FIELD OF THE INVENTION

The present invention relates generally to integrated processes for producing ethanol from methanol via an acetic acid intermediate. In particular, the present invention relates to the integrated ethanol process in which halides, such as methyl iodide, are removed from the acetic acid intermediate that is hydrogenated to ethanol.

BACKGROUND OF THE INVENTION

Ethanol for industrial use is conventionally produced from petrochemical feed stocks, such as oil, natural gas, or coal; from feed stock intermediates, such as syngas; or from starchy materials or cellulose materials, such as corn and sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are often converted to ethanol by fermentation. However, fermentation is typically used for consumer production of ethanol. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. In the reduction of an alkanoic acid, such as acetic acid, water may be formed in an equal molar ratio with ethanol.

Several processes that produce ethanol from acetic acid, and esters, including methyl acetate and ethyl acetate, are described in the literature.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

WO2009063174 describes a continuous process for the production of ethanol from a carbonaceous feedstock. The carbonaceous feedstock is first converted to synthesis gas which is then converted to ethanoic acid, which is then esterified and which is then hydrogenated to produce ethanol.

WO2009009320 describes an indirect route for producing ethanol. Carbohydrates are fermented under homoacidogenic conditions to form acetic acid. The acetic acid is esterified with a primary alcohol having at least 4 carbon atoms and hydrogenating the ester to form ethanol.

US Pub. No. 20110046421 describes a process for producing ethanol comprising converting carbonaceous feedstock to syngas and converting the syngas to methanol. Methanol is carbonylated to ethanoic acid, which is then subjected to a two stage hydrogenation process. First the ethanoic acid is converted to ethyl ethanoate followed by a secondary hydrogenation to ethanol.

U.S. Pat. No. 7,884,253 describes a process for producing ethanol by converting syngas to methanol and catalytically converting the methanol into acetic acid. The acetic acid along with methanol is esterified to generate an acetate. The acetate is reduced with hydrogen to produce ethanol.

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), The Cativa™ Process for the Manufacture of Acetic Acid, *Platinum Metals Review*, 44 (3): 94-105, the entire content and disclosure of which is hereby incorporated by reference.

The crude acetic acid product from the reactor is processed in a purification section to remove impurities and recover acetic acid. These impurities, which may be present in trace amounts, affect the quality of acetic acid, especially as the impurities are circulated through the reaction process, which, among other things, can result in the buildup of these impurities over time. Conventional purification techniques to remove these impurities include treating the acetic acid product streams with oxidizers, ozone, water, methanol, activated-carbon, amines, and the like. The treatments may also be combined with the distillation of the crude acetic acid product. However, the additional treatment of the final product adds cost to the process, and distillation of the treated acetic acid product can result in additional impurities being formed.

Processes for removing these impurities may also remove compounds in the reaction medium, such as the halogen promoter. Several processes have been taught for recovering the halogen promoter including treatment of vented streams and extraction.

Treatment of vented streams allows recovery of halogen promoters. For example, U.S. Publication No. 2009/0270651 discloses a methanol carbonylation system that includes an absorber tower adapted for receiving a vent gas stream and removing methyl iodide therefrom with a scrubber solvent, the absorber tower being coupled to first and second scrubber solvent sources which are capable of supplying different first and second scrubber solvents. A switching system including valves alternatively provides first or second scrubber solvents to the absorber tower and returns the used solvent and absorbed material to the carbonylation system to accommodate different operating modes.

Extraction may also recover halogen promoters from the carbonylation products. For example, U.S. Pat. No. 4,908,477 discloses separating organic iodine compounds from carbonylation products of methanol, methyl acetate and dimethyl ether and from mixtures of such carbonylation products by a process wherein the iodine compounds are removed by liquid phase extraction with a non-aromatic hydrocarbon.

While the above-described processes have been successful in reducing and/or removing impurities from the carbonylation system, further improvements can still be made for removing and recovering the halogen promoters, thus allowing a feed stream substantially free of halogen promoter to be fed to a hydrogenation reactor.

SUMMARY OF THE INVENTION

In a first embodiment, the present invention is directed to a method of producing ethanol comprising the steps of reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst; extracting at least a portion of the reaction solution or a derivative thereof with at least one hydrophobic extractant to obtain an acetic acid intermediate that is substantially free of methyl iodide; introducing the acetic acid intermediate into a second reactor in the presence of a second catalyst to form a crude ethanol product; and recovering ethanol from the crude ethanol product. The derivative of the reaction solution may be obtained from a light ends column and/or a permanganate reducing compound removal system.

In another embodiment, the present invention is directed to a process for producing ethanol, the process comprising the steps of: reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst; flashing the reaction solution to obtain a vapor stream; extracting a condensed portion of the vapor stream with at least one hydrophobic extractant to obtain an acetic acid intermediate that is substantially free of methyl iodide; introducing the acetic acid intermediate into a second reactor in the presence of a second catalyst to form a crude ethanol product; and recovering ethanol from the crude ethanol product.

In yet another embodiment, the present invention is directed to a process for producing ethanol, the process comprising the steps of: reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst; flashing the reaction solution to obtain a vapor stream; separating the vapor stream in a light ends column to yield an acetic acid sidestream and an overhead comprising one or more permanganate reducing compounds, methyl acetate, methanol, water, and methyl iodide, wherein the permanganate reducing compounds are selected from the group consisting of acetaldehyde, acetone, methyl ethyl ketone, butyraldehyde, crotonaldehyde, 2-ethyl crotonaldehyde, 2-ethyl butyraldehyde, the aldol condensation products thereof, and mixtures thereof; extracting a portion of the acetic acid sidestream with at least one hydrophobic extractant to obtain an acetic acid intermediate that is substantially free of methyl iodide; introducing the acetic acid intermediate into a second reactor in the presence of a second catalyst to form a crude ethanol product; and recovering ethanol from the crude ethanol product.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to integrated processes for making ethanol from methanol. In one embodiment, the process includes a step of carbonylating methanol in a carbonylation system in the presence of a carbonylation catalyst under conditions effective to form acetic acid. The carbonylation catalyst may comprise a Group VIII metal and a promoter, such as a halide. In commercial production of acetic acid, the promoter may comprise methyl iodide. To maintain efficiencies in the acetic acid production, methyl iodide is removed and returned to the carbonylation reactor. However, when integrating acetic acid production and ethanol production, it may be possible to use an acetic acid intermediate stream that contains more water, e.g., more than 0.15 wt. % water, or other impurities, such as aldehydes, than higher grade acetic acid. This reduces the energy required to separate the acetic acid.

However, a reduced separation may cause methyl iodide to be present in the acetic acid intermediate that is fed to the hydrogenation reactor. Without being bound by theory, it is believed that halides may cause the catalyst to deactivate. The presence of halides may be harmful to the hydrogenation catalyst resulting in loss of catalytic function. In addition, removing halides, even if not harmful to the particular type of catalyst, also advantageously reduces the concentration of such impurities in the final ethanol product that is ultimately recovered. Furthermore, it is advantageous to retain methyl iodide within the carbonylation system and not introduce another compound into the hydrogenation system.

The acetic acid intermediate that contains a reduced amount of methyl iodide is subsequently hydrogenated in a hydrogenation system in the presence of a hydrogenation catalyst to form a crude ethanol product comprising ethanol and water.

Figure 1:
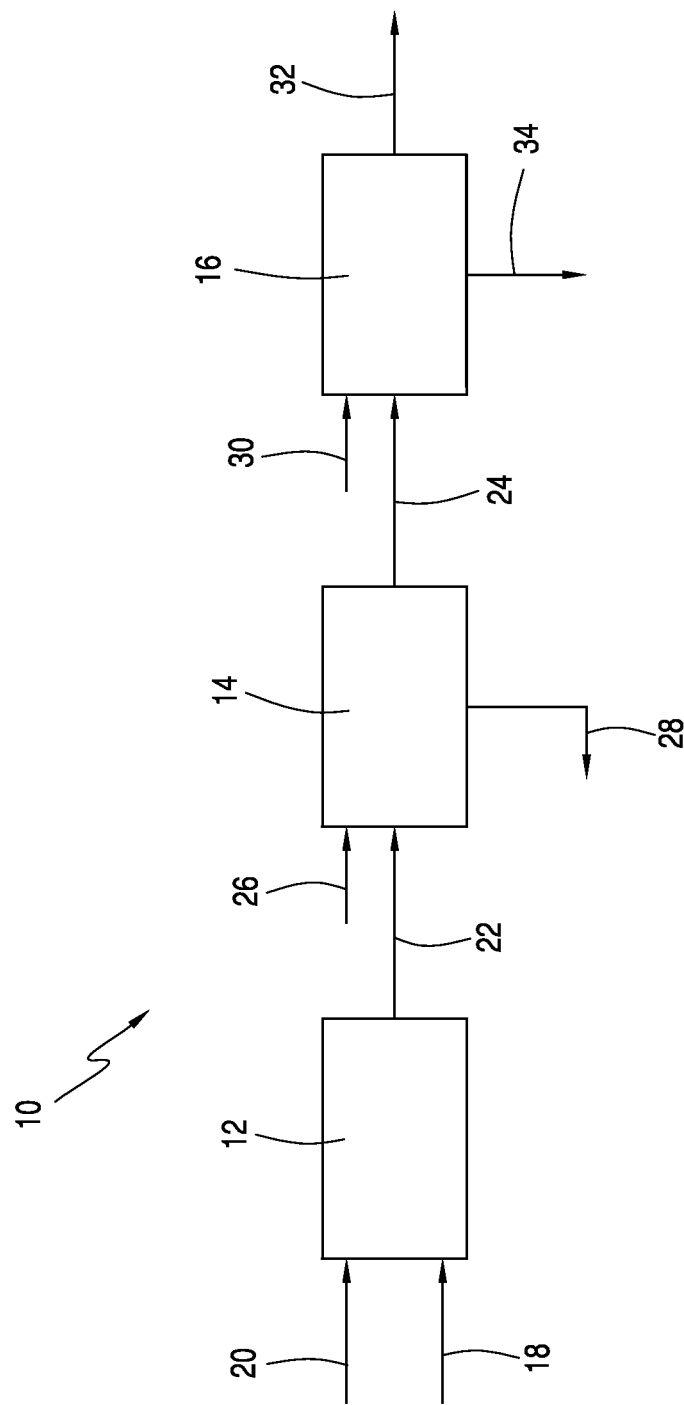
FIG. 1 is a schematic diagram of an integrated system for forming ethanol from methanol via an acetic acid intermediate in accordance with one embodiment of the present invention.

FIG. 1 illustrates an exemplary integrated process 10 in accordance with one embodiment of the present invention. Process 10 comprises carbonylation system 12, halide extraction 14, and hydrogenation system 16. Carbonylation system 12 receives a reactant 18, such as methanol or derivatives thereof, and carbon monoxide feed 20. Methanol and carbon monoxide are reacted in carbonylation system 12 to form acetic acid stream 22. Acetic acid stream 22 may comprise water in amounts of up to 25 wt. %, e.g., up to 20 wt. % water, or up to 10 wt. % water. In terms of ranges, acetic acid stream 22 may comprise from 0.15 wt. % to 25 wt. % water, e.g., from 0.2 wt. % to 20 wt. %, from 0.5 to 15 wt. %, or from 4 wt. % to 10. wt. %. Acetic acid stream 22 is passed through halide extraction 14 to reduce the concentration of halides in the raffinate, e.g., acetic acid intermediate 24. The concentration of halide impurities in acetic acid intermediate 24 may vary, but generally is less than 10 wppm, e.g., from 5 wppb to 500 wppb, e.g., from 10 wppb to 200 wppb, or from 10 wppb to 100 wppb.

In some embodiments, a derivative stream from carbonylation system 12, such as an aldehyde-enriched stream, may pass through halide extraction 14 to remove halide impurities. Halide extraction 14 is a liquid-liquid extraction.

In one embodiment, the halide impurities are removed from the acetic acid intermediate 24 using an extractant 26, which may be selected from the group consisting of $C_5$ to $C_{16}$ alkanes and combinations thereof. Preferably the extractant is hydrophobic and does not extract acetic acid and/or acetaldehyde. In some embodiments, the extractant is a $C_6$ to $C_{16}$ and more preferably $C_8$ to $C_{12}$ alkane. In some embodiments, the extractant is decane, dodecane, or combinations thereof. Methyl iodide stream 28 may be recovered and returned to the carbonylation system 12. In one embodiment, at least 70% of the halide impurities from the acetic acid stream 22 are removed in halide extraction 14, e.g., more preferably at least 85% or at least 95%.

Acetic acid intermediate 24 is fed, more preferably directly fed, to hydrogenation system 16. Hydrogenation system 16 also receives hydrogen feed 30. In hydrogenation system 16, acetic acid and organics are hydrogenated to form a crude ethanol product comprising ethanol and other compounds such as water, ethyl acetate, and acetic acid. Hydrogenation system 16 further comprises one or more separation units, e.g., distillation columns and/or extraction units (not shown in FIG. 1), for separately recovering ethanol from the crude ethanol product. An ethanol product stream 32 is then recovered from hydrogenation system 16. A water stream 34 may also be obtained from the hydrogenation system 16 and purged as necessary. A portion of water stream 34 may be used as an extractant in either the carbonylation system 12 and/or hydrogenation system 16. In one embodiment, ethanol product stream 32 and water stream 34 are substantially free of methyl iodide.

In addition to integrating the water stream between the hydrogenation system 16 and carbonylation system 12, the process may also be integrated with methods for producing acetic acid and/or methods for producing methanol. For example, acetic acid may be produced from methanol, and thus ethanol production according to embodiments of the present invention may be produced from methanol. In one embodiment, the present invention comprises producing methanol from syngas, carbonylating the methanol to form acetic acid, and reducing acetic acid to form an alcohol, namely ethanol. In still another embodiment, the present invention comprises producing ethanol from a carbon source, such as coal, biomass, petroleum, or natural gas, by converting the carbon source to syngas, followed by converting the syngas to methanol, carbonylating the methanol to form acetic acid, and reducing acetic acid to form ethanol. In still another embodiment, the present invention comprises producing ethanol from a carbon source, such as coal, biomass, petroleum, or natural gas, by converting the carbon source to syngas, separating the syngas into a hydrogen stream and a carbon monoxide stream, carbonylating a methanol with the carbon monoxide stream to form acetic acid, and reducing acetic acid to form ethanol. In addition, methanol may be produced from the syngas.

In some embodiments, in addition to the extraction, a guard bed may be used to remove halides and/or sulfur compounds as described in U.S. application Ser. No. 13/078,751, filed on Apr. 1, 2011, the entire contents and disclosure of which is hereby incorporated by reference. The guard bed may include any type of ion exchange resin known in the art. The resins used in the present invention may include metal exchanged functional groups as described in U.S. Pat. Nos. 5,220,558 and 4,615,806, the entireties of which are hereby incorporated by reference. For example, ion exchange resins or other suitable substrates may be prepared for use in connection with the present invention by exchanging anywhere from about 1 to about 99 percent of the active sites of the resin to the silver, palladium, or mercury form by contacting the resin with a silver, palladium, or mercury salt. The silver form, e.g., silver functionalized, is particular preferred for the removal of halogen contaminants. In some embodiments, the ion exchange resin is functionalized with a co-precipitate to the impurity contained in the stream. The metal loading on the resin may vary, and preferably at least 1% of the active sites are occupied, and more preferably from 10 to 90% of the active sites, e.g., 30 to 70%. See, for example, U.S. Pat. No. 6,225,498, the entirety of which is incorporated herein by reference, which discloses methods of removing organic iodides from non-aqueous organic media comprising contacting the organic media with a silver or mercury exchanged cationic ion exchange substrate at a temperature greater than about 50° C. See also U.S. Pat. Nos. 5,801,279; 5,416,237; 5,227,524; and 5,139,981; and EP0685445, the entireties of which are incorporated herein by reference.

Various carbonylation systems and hydrogenation systems may be used in the processes of the present invention. Exemplary materials, catalysts, reaction conditions, and separation processes that may be used in the carbonylation and hydrogenation systems employed in the present invention are described further below.

Carbonylation System

In the carbonylation process, methanol is reacted with carbon monoxide in the presence of a carbonylation reactor under conditions effective to form acetic acid. In some embodiments, some or all of the raw materials for the carbonylation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol mixture, as described in further detail below, may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with the hydrogenation system as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The carbonylation of methanol, or another carbonylatable reactant, including, but not limited to, methyl acetate, methyl formate, dimethyl ether, or mixtures thereof, to acetic acid preferably occurs in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259, the entirety of which is incorporated herein by reference.

Without being bound by theory, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The halogen-containing catalyst promoter of the catalyst system comprises a halogen compound, typically an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

However, methyl iodide may cause corrosion and may poison the reduction catalyst in the hydrogenation reactor. Embodiments of the present invention advantageously increase the amount of methyl iodide that is recovered from alkyl purge stream in the carbonylation process. In one preferred embodiment, substantially no methyl iodide is fed to the hydrogenation reactor and the methyl iodide is recovered from the carbonylation system, thereby reducing costs and improving efficiency of the integrated process.

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at concentrations well below that which has heretofore been thought practical for achieving sufficient reaction rates. It has previously been taught that in rhodium-catalyzed carbonylation reactions of the type set forth in this invention, the addition of water exerts a beneficial effect upon the reaction rate. See, e.g., U.S. Pat. No. 3,769,329, incorporated herein by reference in its entirety. Thus, commercial operations are commonly run at water concentrations of at least about 14 wt. %. Accordingly, it has been quite unexpected that reaction rates substantially equal to and above reaction rates obtained with such comparatively high levels of water concentration can be achieved with water concentrations below 14 wt. % and as low as about 0.1 wt. %.

In accordance with the carbonylation process most useful to manufacture acetic acid according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously. See, e.g., U.S. Pat. No. 5,001,259, incorporated herein by reference in its entirety. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process most useful in this invention, the additional iodide ion over and above the iodide ion present as hydrogen iodide is generally present in the catalyst solution in amounts such that the total iodide ion concentration is from about 2 to about 20 wt. % and the methyl acetate is generally present in amounts of from about 0.5 to about 30 wt. %, and the methyl iodide is generally present in amounts of from about 5 to about 20 wt. %. The rhodium catalyst is generally present in amounts of from about 200 to about 2000 parts per million (ppm).

Typical reaction temperatures for carbonylation will be from 150 to 250° C., with the temperature range of 180 to 220° C. being a preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

In the carbonylation of methanol, PRC's such as acetaldehyde and PRC precursors may be formed as a byproduct, and as a result, the carbonylation system preferably includes a PRC Removal System (PRS) for removing such PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof. Thus, in some embodiments, the invention relates to processes for reducing and/or removing PRC's or their precursors from intermediate streams during the formation of acetic acid by said carbonylation processes.

In some embodiments, the present invention relates to a process in which a condensed light phase from a light ends column overhead is subjected to a distillation step to obtain an overhead that is subjected to a water extraction step to selectively reduce and/or remove PRC's from the process. In one embodiment, the distillation step in the PRS includes a single distillation column as described in U.S. Pat. No. 7,855,306, the entirety of which is incorporated herein by reference, while in other embodiments the distillation step may include two or more distillation steps as described, for example, in U.S. Pat. No. 6,143,930, the entirety of which is incorporated herein by reference. Similarly, in one embodiment, the extraction step in the PRS includes a single extraction unit, while in other embodiments, multiple extraction units employing the same or different extractants, may be employed, as described for example, in U.S. Pat. No. 7,223,886, the entirety of which is incorporated herein by reference. Although the PRS is illustrated and described herein as having a single distillation column and a single extraction unit, it should be understood that the principles of the invention may be employed with separation systems having multiple distillation columns and/or multiple extraction units.

Figure 2:
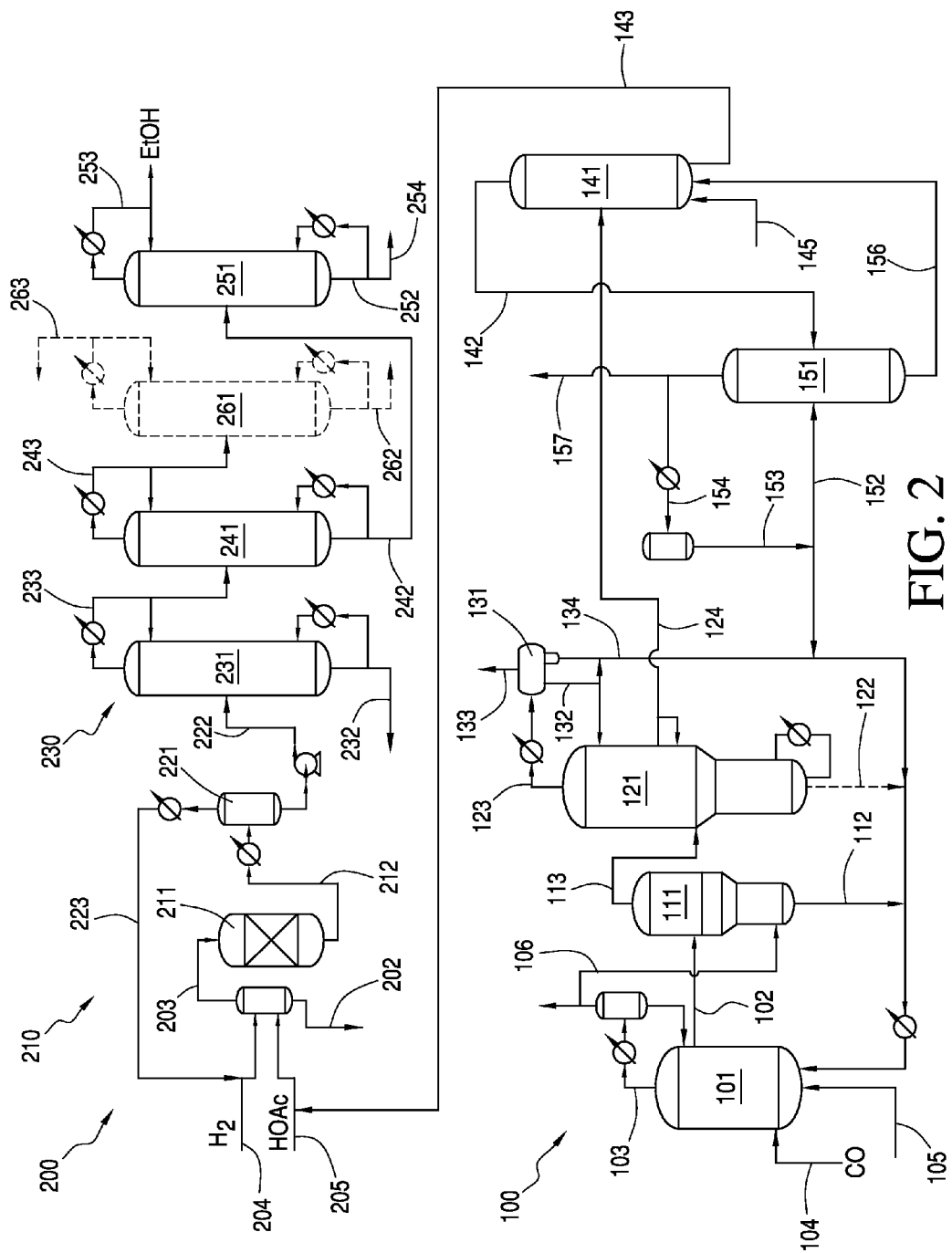
FIG. 2 is a schematic diagram of an integrated ethanol production system in which halides are extracted from the acetic acid side stream in accordance with one embodiment of the present invention.

A typical reaction and acetic acid recovery system 100 that is used for the iodide-promoted rhodium catalyzed carbonylation of methanol to acetic acid is shown in FIG. 2 and includes a liquid phase carbonylation reactor 101, flasher 111 and light ends column 121. Carbon monoxide feed 104 and a reactant feed 105, comprising methanol, methyl acetate, methyl formate, dimethyl ether, or mixtures thereof, are fed to reactor 101. Carbonylation product is continuously withdrawn in line 102 and is provided to the flasher 111 where a volatile ("vapor") overhead stream 113 comprising acetic acid and a less volatile catalyst phase 112 comprising a catalyst-containing solution are obtained. Reactor 101 may be vented and a portion of the carbon monoxide may be directed to flasher 111 to stabilize the catalyst therein via line 106. The volatile overhead stream 113 comprising acetic acid is provided to the light ends column 121 where distillation yields an acetic acid product that is removed via sidestream 124 and an overhead distillate stream 123 (hereafter "low-boiling overhead vapor stream").

The carbonylation reactor is typically either a stirred vessel or bubble-column type within which the reacting liquid or slurry contents are maintained automatically at a constant level. Into this reactor, fresh methanol, carbon monoxide and sufficient water as needed to maintain at least a finite concentration of water in the reaction medium are continuously introduced. Also introduced into the reactor is a recycled catalyst solution, such as from the flasher base, a recycled methyl iodide phase, a recycled methyl acetate phase, and a recycled aqueous acetic acid phase. A recycled phase may contain one or more of the foregoing components.

Distillation systems are employed that provide means for recovering the crude acetic acid and recycling catalyst solution, methyl iodide, methyl acetate, and other system components within the process. In a typical carbonylation process, carbon monoxide is continuously introduced into the carbonylation reactor, desirably below the agitator, which is used to stir the contents. The gaseous feed is thoroughly dispersed through the reacting liquid by this stirring means. A gaseous purge stream is desirably vented from the reactor to prevent buildup of gaseous by-products and to maintain a set carbon monoxide partial pressure at a given total reactor pressure. The temperature of the reactor is controlled and the carbon monoxide feed is introduced at a rate sufficient to maintain the desired total reactor pressure.

Liquid product is drawn off from the carbonylation reactor at a rate sufficient to maintain a constant level therein and is introduced to the flasher. In the flasher, a catalyst-containing solution (catalyst phase) is withdrawn as a base stream (predominantly acetic acid containing the rhodium and the iodide salt along with lesser quantities of methyl acetate, methyl iodide, and water), while a vapor overhead stream comprising acetic acid is withdrawn overhead. The vapor overhead stream comprising acetic acid also contains methyl iodide, methyl acetate, and water. Dissolved gases exiting the reactor and entering the flasher comprise a portion of the carbon monoxide and may also contain gaseous by-products such as methane, hydrogen, and carbon dioxide. Such dissolved gases exit the flasher as part of the overhead stream. As explained above, the overhead stream is directed to the light ends column 121 as stream 113.

It has been disclosed in U.S. Pat. Nos. 6,143,930 and 6,339,171 that there is generally a higher concentration of the PRC's and in particular acetaldehyde content in the low-boiling overhead vapor stream 123 exiting column 121 than in the high-boiling residue stream 122 exiting column 121. Low-boiling overhead vapor stream 123 will typically contain methyl iodide, acetaldehyde, methyl acetate, acetic acid and water. Low-boiling overhead vapor stream 123 is condensed and directed to overhead receiving decanter 131. Conditions are desirably maintained in the process such that low-boiling overhead vapor stream 123 is chilled to a temperature sufficient to condense and separate the condensable methyl iodide, acetaldehyde, methyl acetate, other carbonyl components, and water into two phases. A portion of stream 123 may include non-condensable gases such as carbon dioxide, hydrogen and the like that can be vented as shown in stream 133 in FIG. 2.

The condensed light phase 132 in decanter 131 will generally comprise water, acetic acid, acetaldehyde, methyl iodide, methanol and methyl acetate. The condensed heavy phase 134 in decanter 131 may be returned to reactor 101, and optionally a portion of a light phase may be returned to light ends column 121 or to reactor 101 after combination with line 134. While either phase of the light ends overhead, i.e., low-boiling overhead vapor stream 123, may be subsequently processed to remove the PRC's, primarily acetaldehyde, the PRC's are preferably removed from the condensed light phase 132.

Thus, the condensed heavy phase 134 in the decanter 131 can be conveniently recirculated, either directly or indirectly, to the reactor 101, and optionally recirculated with a portion of the light phase 132. For example, a portion of this condensed heavy phase 134 can be recirculated to the reactor, with a slip stream, generally a small amount, e.g., 25 vol. %, preferably less than about 20 vol. %, of the heavy phase 134 being directed to a carbonyl treatment process. This slip stream of the heavy phase 134 may be treated individually or may be combined with the condensed light phase 132 for further distillation and extraction of carbonyl impurities.

Acetic acid sidestream 124 is withdrawn from light ends column 121 and introduced to extractor 141 to remove halides, and in particular methyl iodide. A primary concern in the extraction step that separates methyl iodide is the relative solubility of methyl iodide in water. Acetic acid side stream 124 may comprise water in amounts of up to 25 wt. %, e.g., greater than 0.15 wt. %. The solubility of methyl iodide in water increases, with a concomitant loss of methyl iodide from the process system, with increasing levels of methyl acetate and/or methanol. At high enough methyl acetate and/or methanol levels, phase separation of methyl iodide in the extraction may not occur. Thus, it is desirable that acetic acid side stream 124 contain methanol and methyl acetate at a combined concentration of less than about 10 wt. %, more desirably less than about 5 wt. %, even more desirably less than about 2 wt. %, and even more desirably less than about 1.5 wt. %.

In extractor 141, methyl iodide is extracted with the extractant from extractant feed 145. Extraction may be either a single stage or multistage extraction and any equipment used to conduct such extractions can be used in the practice of the present invention. Multistage extraction is preferred. The extractant is preferably selected from the group consisting of $C_5$ to $C_{16}$ alkanes and combinations thereof. As a result of this extraction, sidestream 124 is separated into a raffinate acetic acid intermediate 143, and a stream 142 comprising methyl iodide. Raffinate 143 is an acetic acid intermediate that may be fed to hydrogenation system 200 to produce ethanol, as described herein.

Accordingly, it is desirable that the extraction be conducted at a combination of temperature and pressure such that the extractor contents can be maintained in the liquid state. Moreover, it is desirable to minimize the temperatures to which stream 124 is exposed to minimize the likelihood of polymerization and condensation reactions involving acetaldehyde. In some embodiments, the extraction is conducted at a temperature of from 10° C. to 40° C.

Although the specific compositions of stream 142 may vary widely, it is preferred that a majority of the methyl iodide in line 124 pass through to stream 142. In one embodiment, at least 70% of the methyl iodide passes through to stream 142, e.g., more preferably at least 85% or at least 95%. In a preferred embodiment, about 99% or more of the methyl iodide passes through to stream 142. In one embodiment, acetic acid intermediate in raffinate 143 comprises substantially no methyl iodide.

Stream 142 is directed to removal column 151 to produce a distillate stream and an extractant residue stream in line 156. The distillate stream in line 154 may be purged via line 157 and the remaining portion may be condensed. A portion may be refluxed as necessary, and the remaining portion may be returned to the carbonylation reactor 101.

Figure 3:
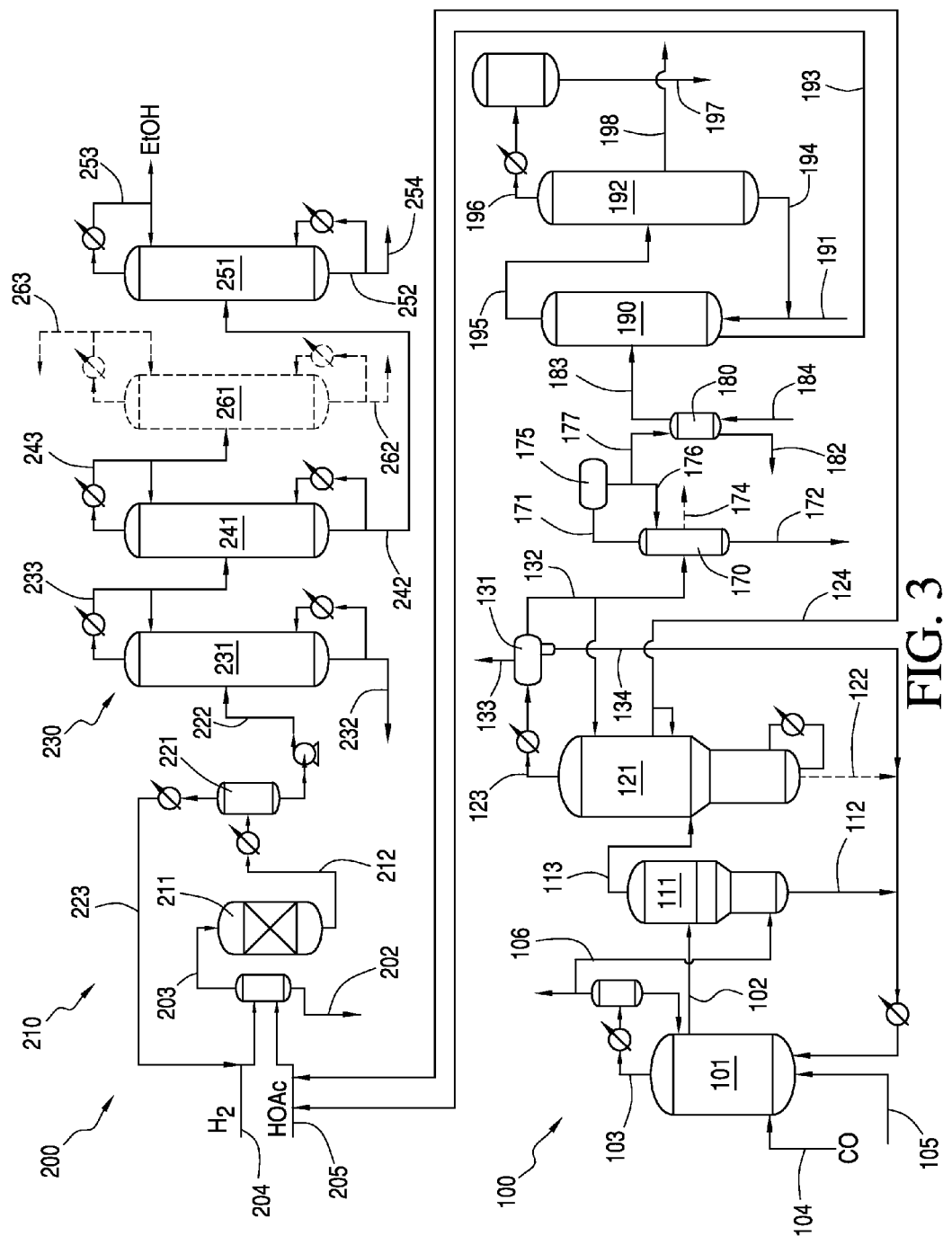
FIG. 3 is a schematic diagram of an integrated ethanol production system in which halides are extracted from the permanganate reducing compound removal system in accordance with one embodiment of the present invention.

In another embodiment, as shown in FIG. 3, a derivative stream may pass through a halide extraction and be fed to the hydrogenation system. The derivative stream may be fed in combination with an acetic acid sidestream 124 or alone. Preferably, the derivative stream is an aldehyde-enriched stream. As stated above, light phase 132 may contain PRC's, methyl iodide, methanol and/or methyl acetate. To remove PRC's from the system, light phase 132 is fed to one or more distillation columns 170 (one is shown), which serve to form a second vapor phase 171 enriched in acetaldehyde, but also containing methyl iodide due to the similar boiling points of methyl iodide and acetaldehyde. The second vapor phase stream 171 overhead is enriched with acetaldehyde with respect to the light condensed liquid phase in line 132. The second vapor phase stream 171 is deficient with methyl acetate, methanol, and/or acetic acid (desirably all three) with respect to said light condensed liquid phase in line 132. Second vapor phase 171 is condensed and then extracted with water to reduce and/or remove acetaldehyde. In a preferred embodiment, a portion of the condensed stream is provided in line 176 as reflux to distillation column 170. This can be accomplished, by providing the condensed stream 171 to an overhead receiver 175, from which a portion of condensed stream 171 can be provided to extractor 180 via line 177, or fed back to distillation column 170 via line 176.

In an optional embodiment, sidestream 174, comprising methyl acetate, is also taken from distillation column 170. If used, sidestream 174 allows the distillation column 170 to be operated under conditions desirable for obtaining a higher concentration of acetaldehyde in second vapor phase stream 171 while providing a mechanism for removing methyl acetate that might otherwise build up in the center of distillation column 170 or be pushed into the second vapor phase stream 171 overhead. The sidestream 174 is preferably retained in the process in the process by recirculating to the reactor 101, light ends column 121 or decanter 131.

Further in accordance with this embodiment of the present invention, second vapor phase stream 171 is extracted with water to remove residual PRC's, notably acetaldehyde. Operating without a sidestream 174, the process has been found to achieve the following results respecting the separation capabilities of distillation column 170, as shown in Table 1.

TABLE 1

EXEMPLARY STREAM COMPOSITIONS WITHOUT SIDESTREAM

| Component | Stream 132 (wt. %) | Stream 171 (wt. %) | Stream 172 (wt. %) |
|---|---|---|---|
| Methyl iodide | 1.5 | 74.5 | <0.1 |
| Methyl acetate | 6.0 | 1.4 | 6.1 |
| Methanol | 4.0 | 0.2 | 4.1 |
| Acetic acid | 15 | <0.1 | 15.3 |
| Water | 73 | 1.6 | 74.5 |
| Acetaldehyde | 0.5 | 22.2 | 0.1 |

Extraction with water can be either a single stage or multistage extraction and any equipment used to conduct such extractions can be used in the practice of the present invention. Multistage extraction is preferred. For example, extraction can be accomplished by combining stream 177 with water. Multiple mixer/separator combinations can be operated in series to obtain a multistage extraction. Optionally, and desirably, multistage extraction is accomplished in a single vessel having a series of trays. The vessel may be equipped with paddle(s) or other mechanisms for agitation to increase extraction efficiency. In such a multistage extraction vessel, stream 177 is desirably provided proximate to one end of the vessel 180 with the extractant 184 being provided proximate to the other end of the vessel 180 or such other location to obtain a countercurrent flow.

The mutual solubility between the two phases in the extraction can increase with temperature. Accordingly, it is desirable that the extraction be conducted at a combination of temperature and pressure such that the extractor contents can be maintained in the liquid state. Moreover, it is desirable to minimize the temperatures to which stream 177 is exposed to minimize the likelihood of polymerization and condensation reactions involving acetaldehyde. Water used in the extraction is desirably from an internal stream so as to maintain water balance within the carbonylation system. In some embodiments, water may be obtained from the hydrogenation section 200. Dimethyl ether (DME) may also be introduced to the extraction to improve the separation of methyl iodide in the extraction, i.e., to reduce the loss of methyl iodide into the aqueous acetaldehyde stream 183. The DME can be introduced to the process or formed in situ.

Acetaldehyde is extracted using an extractant in line 184 to obtain an aqueous acetaldehyde stream 183, also referred to as a derivative stream. Raffinate 182, notably containing methyl iodide, can be purged from the system or recovered for further processing and/or use. The efficiency of the extraction will depend on such things as the number of extraction stages and the water to feed ratio. Extractant in line 184 may comprise water, dimethyl ether, and/or alkanes. When a multistage extractor is used, there may be a different extractant in each stage. When water is used as an extractant, it may be preferable to use a portion of the water of reaction in the hydrogenation process as explained above.

Acetaldehyde stream 183 may be further processed, as shown in FIG. 3. Acetaldehyde stream 183 is directed to second extractor 190 for further separation of methyl iodide from acetaldehyde stream 183. The second extractant in line 191 is preferably different from the first extractant. The second extractant preferably is selected from the group consisting of $C_5$ to $C_{16}$ alkanes and combinations thereof. As a result of this extraction, acetaldehyde stream 183 after extraction is separated into second raffinate stream 193 comprising water and acetaldehyde and an extract stream 195 comprising the extractant and methyl iodide. Second raffinate stream 193 is fed to acetic acid stream 205 for use in the hydrogenation process 200. Although the specific compositions of second raffinate stream 193 may vary widely, second raffinate stream 193 preferably comprises less than 2 wt. % methyl iodide, e.g., less than 1 wt. % methyl iodide or less than 0.5 wt. % or less than 0.1 wt. % or is substantially free of methyl iodide, e.g., less than 10 wppm methyl iodide.

Extracted stream 195 is directed to removal column 192 to produce a distillate stream 196 comprising methyl iodide, a residue stream 194 comprising extractant which is fed into line 191 to be returned to second extractor 190, and an alkyl purge stream 198 which can be further processed or reused. Distillate stream 196 is condensed and may be returned to the reactor or purged from the system via line 197. Distillate stream 196 comprises methyl iodide.

In embodiments employing sidestream 174, the second vapor phase stream 171 overhead is enriched with PRC, notably acetaldehyde, with respect to light condensed liquid phase 132. The second vapor phase stream 171 overhead is deficient with methyl acetate, methanol, and/or acetic acid (desirably all three) with respect to light condensed liquid phase 132. The second vapor phase stream 171 overhead is deficient with methyl acetate, methanol, and/or acetic acid (desirably all three) with respect to said sidestream 174 and, desirably, also with respect to the higher boiling liquid phase residuum stream 172. Desirably, the second vapor phase stream 171 overhead is enriched with PRC's, notably acetaldehyde, with respect to both the sidestream 174 and the higher boiling liquid phase residuum stream 172.

This process has been found to reduce and/or remove PRC's and their precursors, multi-carbon alkyl iodide impurities, and propionic and higher carboxylic acids from the carbonylation process. It has also been shown that acetaldehyde and its derivatives are reduced and/or removed by sufficient amounts such that it is possible to keep the concentration of propionic acid in the acetic acid product below about 500 parts per million by weight, preferably below about 300 wppm, and most preferably below 250 wppm.

In variations of the embodiments of the present invention, it is important to inhibit the formation of various aldehyde related polymers and condensation products in distillation column 170. Acetaldehyde polymerizes to form metaldehyde and paraldehyde. These polymers generally are low molecular weight, less than about 200. Higher molecular weight polymers of acetaldehyde can also form. These higher molecular weight polymers (molecular weight greater than about 1000) are believed to form during processing of the light phase and are viscous and thixotropic. Acetaldehyde can also undergo undesirable aldol condensation reactions.

The formation of these impurities, i.e., metaldehyde and paraldehyde and higher molecular weight polymers of acetaldehyde, can be suppressed by introducing into distillation column 170 a flush stream containing at least water and/or acetic acid.

Figure 4:
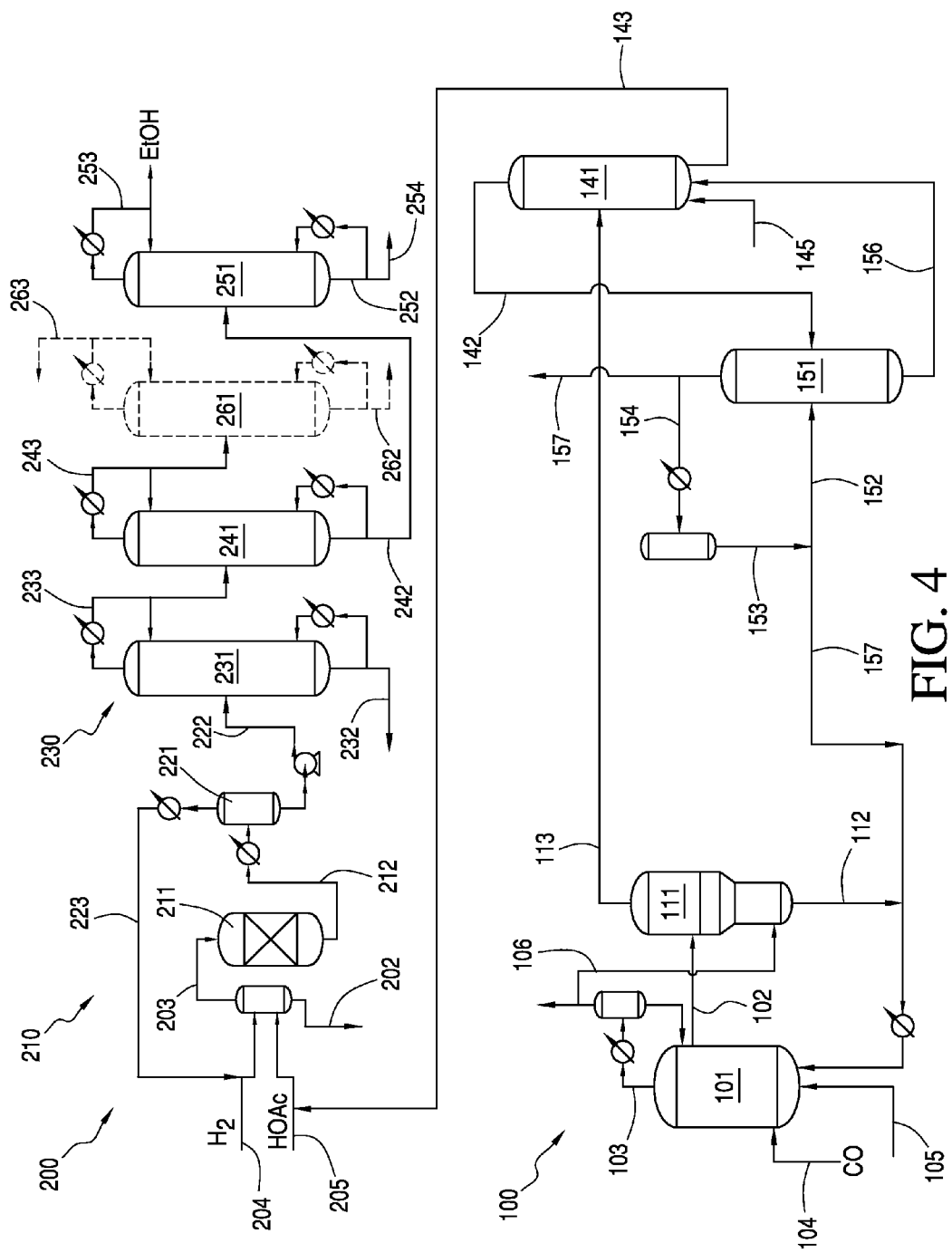
FIG. 4 is a schematic diagram of an integrated ethanol production system in which halides are extracted from the vapor stream of the flasher in accordance with one embodiment of the present invention.

In another embodiment, as shown in FIG. 4, overhead stream 113 from flasher 111 is condensed and directed to extractor 141. Additionally, extractant feed 145 is fed to extractor 141. Extraction may be either a single stage or multistage extraction and any equipment used to conduct such extractions can be used in the practice of the present invention. Multistage extraction is preferred. In extractor 141, methyl iodide is extracted with the extractant from extractant feed 145. The extractant is preferably selected from the group consisting of $C_5$ to $C_{16}$ alkanes and combinations thereof. As a result of this extraction, overhead stream 113 is separated into a raffinate 143 that comprises acetic acid intermediate 143, which may be fed to hydrogenation system 200 and a stream 142 comprising methyl iodide.

Similar to the other embodiments, stream 142 is directed to removal column 151 to produce a distillate stream and an extractant residue stream in line 156. The distillate stream in line 154 may be purged via line 157 and the remaining portion may be condensed. A portion may be refluxed as necessary, and the remaining portion may be returned to the carbonylation reactor 101.

Hydrogenation System

As discussed above, the processes for production ethanol integrate a carbonylation system with a hydrogenation system. The hydrogenation system preferably includes a hydrogenation reactor and a hydrogenation catalyst system effective in converting the acetic acid intermediate to ethanol and water. The hydrogenation system also includes a separation system for separating a crude ethanol product into an ethanol product stream, a water stream, and optionally one or more byproduct streams.

In addition to acetic acid, the acetic acid feed stream that is fed to the hydrogenation reactor may comprise other carboxylic acids and anhydrides, as well as aldehydes and/or ketones, such as acetaldehyde and acetone. Preferably, a suitable acetic acid feed stream comprises one or more compounds selected from the group consisting of acetic acid, acetic anhydride, acetaldehyde, ethyl acetate, and mixtures thereof. These compounds may also be hydrogenated in the processes of the present invention. In some embodiments, the presence of some carboxylic acids, such as propanoic acid or its anhydride, may be beneficial in producing propanol. Water may also be present in the acetic acid feed, in amounts of up to 25 wt. %, e.g., up to 20 wt. % water, or up to 10 wt. % water. Preferably, substantially no methyl iodide is present in the acetic acid feed stream.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the reactor. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a mole percentage based on acetic acid in the feed. For example, acetic acid may have a conversion that is greater than 40%, e.g., greater than 50%, greater than 70% or greater than 90%. The conversion may vary and may be from 40% to 70% in some embodiments and from 85% to 99% in others.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, in the reactor, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol mixture produced by the reactor, before any subsequent processing, such as purification and separation, will typically comprise acetic acid, ethanol and water. Exemplary compositional ranges for the crude ethanol mixture are provided in Table 2. The "others" identified in Table 2 may include, for example, esters, ethers, aldehydes, ketones, alkanes, and carbon dioxide.

TABLE 2

CRUDE ETHANOL MIXTURE COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 10 to 70 | 15 to 60 | 20 to 50 |
| Water | 5 to 40 | 5 to 28 | 10 to 26 | 10 to 22 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Diethyl Acetal | 0.001 to 5 | 0.01 to 3 | 0.1 to 2 | 0.5 to 1.5 |
| Others | 0.1 to 10 | 0.1 to 6 | 0.1 to 4 | — |

In one embodiment, the crude ethanol mixture may comprise acetic acid in an amount less than 20 wt. %, e.g., less than 15 wt. %, less than 10 wt. % or less than 5 wt. %. In terms of ranges, the acetic acid concentration of Table 2 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Figure 5:
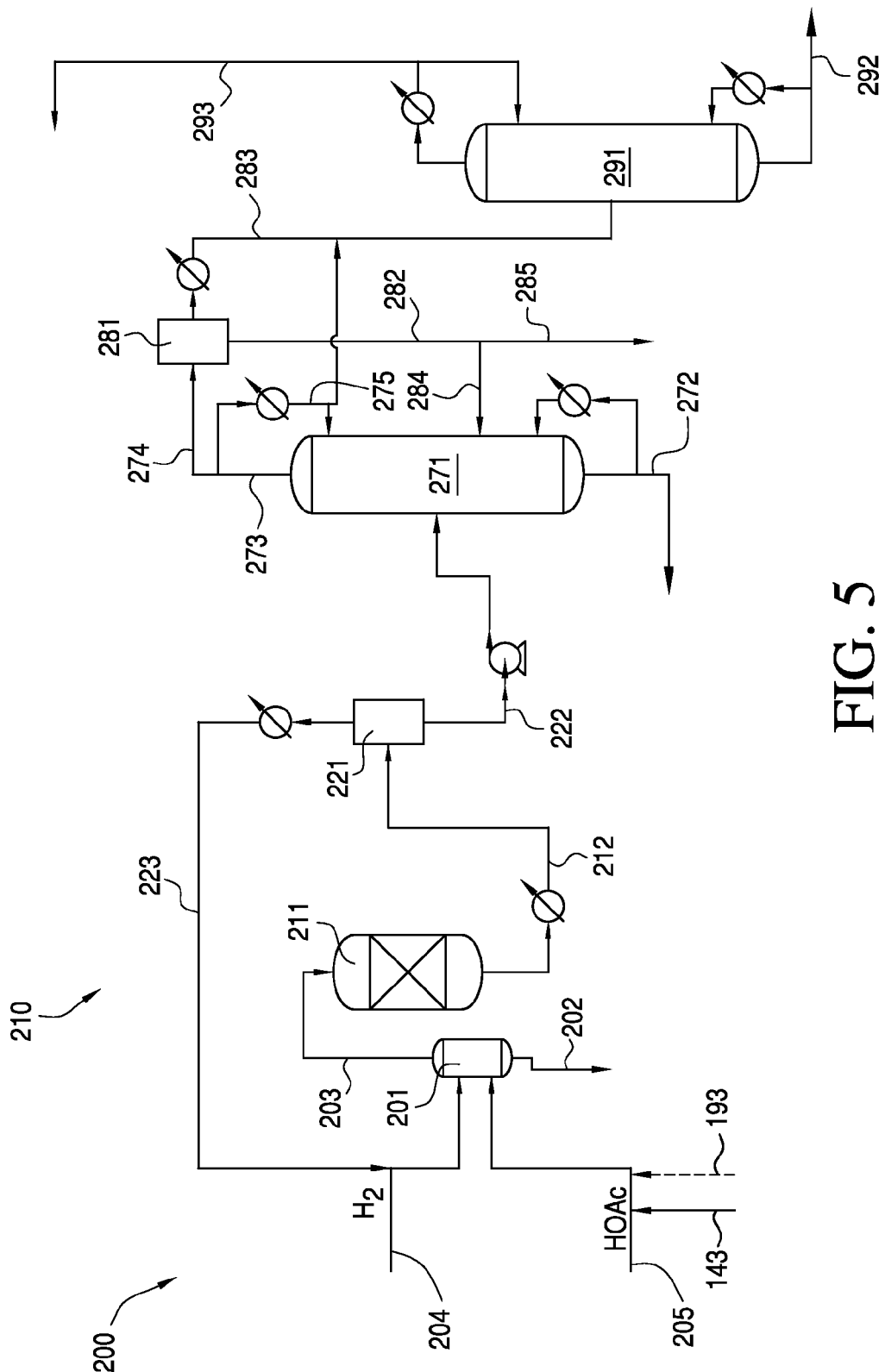
FIG. 5 is a schematic diagram of an ethanol production system having a water removal process in accordance with one embodiment of the present invention.
Figure 6:
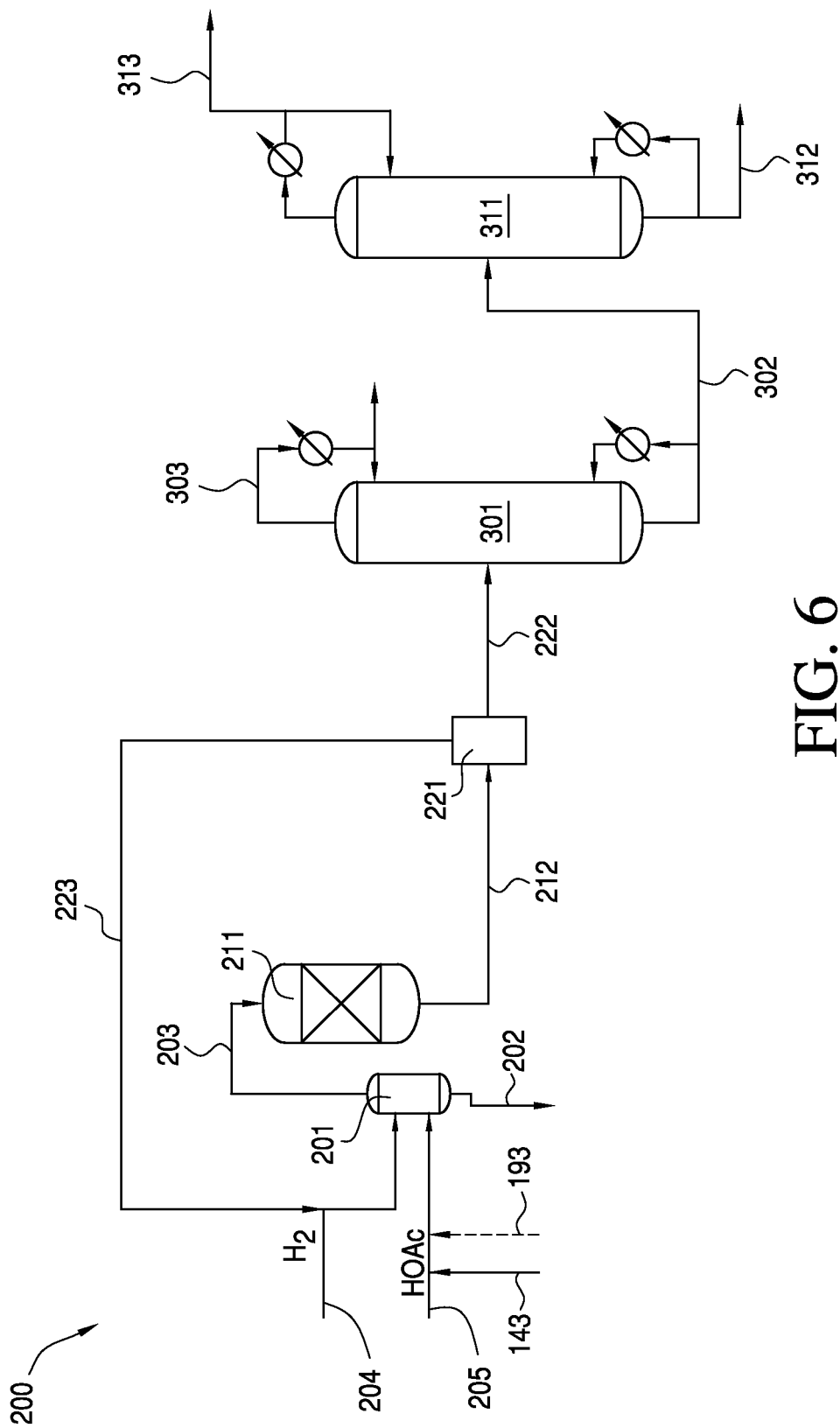
FIG. 6 is a schematic diagram of an ethanol production system having two distillation columns in accordance with one embodiment of the present invention.

Ethanol may be recovered using several different techniques. In FIGS. 2-4, the hydrogenation section 200 separates the crude ethanol mixture using three columns 231, 241, 251 and/or an optional fourth column 261. Other separation systems may also be used with embodiments of the present invention, as shown in FIGS. 5 and 6.

In each of the figures, hydrogenation section 200 includes a reaction zone 210 and a separation zone 230. Acetic acid may be supplied from acetic acid intermediate in line 143 and/or optionally from raffinate 193 and fed via line 205. As indicated above, the acetic acid fed to hydrogenation section 200 is substantially free of methyl iodide. Hydrogen via line 204 is also fed to a vaporizer 201 to create a vapor feed stream in line 203 that is directed to reactor 211. In one embodiment, the feed lines, including streams fed from carbonylation section 100, be combined and jointly fed to vaporizer 201. The temperature of the vapor feed stream in line 203 is preferably from 100° C. to 350° C., e.g., from 120° C. to 310° C. or from 150° C. to 300° C. Any feed that is not vaporized is removed from vaporizer 201 and may be withdrawn as a blowdown stream 202. In addition, although line 203 is shown as being directed to the top of reactor 211, line 203 may be directed to the side, upper portion, or bottom of reactor 211.

Reactor 211 contains the catalyst that is used in the hydrogenation of the carboxylic acid, preferably acetic acid, and other carbonyl compounds, such as ethyl acetate and acetaldehyde. In one embodiment, one or more guard beds (not shown) may be used upstream of the reactor, optionally upstream of vaporizer 201, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol mixture stream is withdrawn, preferably continuously, from reactor 211 via line 212.

The crude ethanol mixture stream in line 212 may be condensed and fed to a separator 221, which, in turn, provides a vapor stream 223 and a liquid stream 222. In some embodiments, separator 221 may comprise a flasher or a knockout pot. The separator 221 may operate at a temperature of from 20° C. to 250° C., e.g., from 30° C. to 225° C. or from 60° C. to 200° C. The pressure of separator 221 may be from 50 kPa to 2000 kPa, e.g., from 75 kPa to 1500 kPa or from 100 kPa to 1000 kPa. Optionally, the crude ethanol mixture in line 212 may pass through one or more membranes to separate hydrogen and/or other non-condensable gases.

The vapor stream 223 exiting separator 221 may comprise hydrogen and hydrocarbons, and may be purged and/or returned to reaction zone 210. When returned to reaction zone 210, vapor stream 223 may be combined with the hydrogen feed 204 and co-fed to vaporizer 201. In some embodiments, the returned vapor stream 223 may be compressed before being combined with hydrogen feed 204.

The liquid stream 222 from separator 221 is withdrawn and pumped to the side of first column 231, also referred to as an "acid separation column." In one embodiment, the contents of liquid stream 222 are substantially similar to the crude ethanol mixture obtained from the reactor, except that the composition has been depleted of hydrogen, carbon dioxide, methane and/or ethane, which are removed by separator 221. Accordingly, liquid stream 222 may also be referred to as a crude ethanol mixture. Exemplary components of liquid stream 222 are provided in Table 3. It should be understood that liquid stream 222 may contain other components, not listed in Table 3.

TABLE 3

COLUMN FEED COMPOSITION
(Liquid Stream 222)

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 5 to 70 |
| Water | 5 to 30 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 3 may include, but are not limited to, ethyl propionate, methyl acetate, isopropyl acetate, n-propyl acetate, n-butyl acetate or mixtures thereof. The "other ethers" in Table 3 may include, but are not limited to, diethyl ether, methyl ethyl ether, isobutyl ethyl ether or mixtures thereof. The "other alcohols" in Table 3 may include, but are not limited to, methanol, isopropanol, n-propanol, n-butanol or mixtures thereof. In one embodiment, the liquid stream 222 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol mixture in line 212 or in liquid stream 222 may be further fed to an esterification reactor, hydrogenolysis reactor, or combination thereof. An esterification reactor may be used to consume residual acetic acid present in the crude ethanol mixture to further reduce the amount of acetic acid that would otherwise need to be removed. Hydrogenolysis may be used to convert ethyl acetate in the crude ethanol mixture to ethanol.

In one preferred embodiment liquid stream 222 is introduced in the lower part of first column 231, e.g., lower half or lower third. In first column 231, acetic acid, a portion of the water, and other heavy components, if present, are removed from the composition in line 232 and are withdrawn, preferably continuously, as residue. Some or all of the residue may be returned and/or recycled back to reaction zone 210 via line 232. Recycling the acetic acid in line 232 to the vaporizer 201 may reduce the amount of heavies that need to be purged from vaporizer 201. Reducing the amount of heavies to be purged may improve efficiencies of the process while reducing byproducts. First column 231 also forms an overhead distillate, which is withdrawn in line 233, and which may be condensed and refluxed, for example, at a ratio of from 10:1 to 1:10, e.g., from 3:1 to 1:3 or from 1:2 to 2:1. The distillate in line 233 comprises primarily ethanol, as well as water, ethyl acetate, acetaldehyde, and/or diethyl acetal. For example, distillate may comprise from 20 to 75 wt. % ethanol and 10 to 40 wt. % ethanol. Preferably, the concentration of acetic acid in the distillate is less than 2 wt. %, e.g., less than 1 wt. % or less than 0.5 wt. %.

In one embodiment, the pressure of first column 231 may range from 0.1 kPa to 510 kPa, e.g., from 1 kPa to 475 kPa or from 1 kPa to 375 kPa. When first column 231 is operated under standard atmospheric pressure, the temperature of the residue exiting in line 232 preferably is from 95° C. to 120° C., e.g., from 110° C. to 117° C. or from 111° C. to 115° C. The temperature of the distillate exiting in line 233 preferably is from 70° C. to 110° C., e.g., from 75° C. to 95° C. or from 80° C. to 90° C.

As shown, the first distillate in line 233 is introduced to the second column 241, also referred to as the "light ends column," preferably in the middle part of column 241. Preferably the second column 241 is an extractive distillation column, and an extraction agent is added thereto via line 244. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 233 that is fed to the second column 241 comprises ethanol, water, and ethyl acetate. These compounds tend to form binary and ternary azeotropes, which decrease separation efficiency. In one embodiment the extraction agent comprises a portion of the third residue in line 252. Preferably, the recycled third residue in line 244 is fed to second column 241 at a point higher than the first distillate in line 233. In one embodiment, the recycled third residue is fed in line 244 near the top of second column 241 or fed, for example, above the feed in line 244 and below the reflux line from the condensed overheads. In a tray column, the third residue in line 244 is continuously added near the top of the second column 241 so that an appreciable amount of the third residue is present in the liquid phase on all of the trays below. In another embodiment, the extraction agent is fed from a source outside of the process to second column 241. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as: water from an external source; dimethylsulfoxide; glycerine; diethylene glycol; 1-naphthol; hydroquinone; N,N'-dimethylformamide; 1,4-butanediol; ethylene glycol-1,5-pentanediol; propylene glycol-tetraethylene glycol-polyethylene glycol; glycerine-propylene glycol-tetraethylene glycol-1,4-butanediol; ethyl ether; methyl formate; cyclohexane; N,N'-dimethyl-1,3-propanediamine; N,N'-dimethylethylenediamine; diethylene triamine; hexamethylene diamine; 1,3-diaminopentane; an alkylated thiopene; dodecane; tridecane; tetradecane; and chlorinated paraffins, may be added to second column 241. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 252 and co-fed to the second column 241. The additional extraction agent may also be added separately to the second column 241. In one aspect, the extraction agent comprises an extraction agent, e.g., water, derived from an external source and none of the extraction agent is derived from the third residue.

Second column 241 may be a tray or packed column. In one embodiment, second column 241 is a tray column having from 5 to 120 trays, e.g., from 15 to 80 trays or from 20 to 70 trays. The temperature of second column 241 at atmospheric pressure may vary. Second column 241 may operate at a pressure ranging from 0.1 kPa to 510 kPa, e.g., from 1 kPa to 475 kPa or from 1 kPa to 375 kPa. In one embodiment second residue exiting in line 242 preferably is at a temperature from 60° C. to 90° C., e.g., from 70° C. to 90° C. or from 80° C. to 90° C. The temperature of the second distillate exiting in line 243 from second column 241 preferably is from 50° C. to 90° C., e.g., from 60° C. to 80° C. or from 60° C. to 70° C.

The second residue in line 242 comprises ethanol and water. The second residue may comprise less than 3 wt. % ethyl acetate, e.g., less than 1 wt. % ethyl acetate or less than 0.5 wt. % ethyl acetate. The second distillate in line 243 comprises ethyl acetate, acetaldehyde, and/or diethyl acetal. In addition, minor amounts of ethanol may be present in the second distillate. The weight ratio of ethanol in the second residue to second distillate preferably is at least 3:1, e.g., at least 6:1, at least 8:1, at least 10:1 or at least 15:1.

All or a portion of the third residue is recycled to the second column. In one embodiment, all of the third residue may be recycled until process reaches a steady state at which point a portion of the third residue may be recycled with the remaining portion being purged from the system. As the third residue is recycled, the composition of the second residue will tend to decrease in ethanol concentration. As the third residue is recycled, the composition of the second residue comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column 251, which is highly beneficial in ultimately forming a highly pure ethanol product.

As shown, the second residue from second column 241, which comprises ethanol and water, is fed via line 242 to third column 251, also referred to as the "product column." More preferably, the second residue in line 242 is introduced in the lower part of third column 251, e.g., lower half or lower third. Third column 251 recovers ethanol, which preferably is substantially pure with respect to organic impurities and other than the azeotropic water content, as the distillate in line 253. The distillate of third column 251 preferably is refluxed as shown in FIG. 2, for example, at a reflux ratio of from 1:10 to 10:1, e.g., from 1:3 to 3:1 or from 1:2 to 2:1. The third residue in line 252, which comprises primarily water, preferably is returned to the second column 241 as an extraction agent as described above. In one embodiment, a first portion of the third residue is recycled to the second column in line 244 and a second portion is purged and removed from the system via line 254. In one embodiment, once the process reaches steady state, the second portion of water to be purged is substantially similar to the amount of water formed in the hydrogenation of acetic acid. In one embodiment, a portion of the third residue may be used to hydrolyze any other stream, such as one or more streams comprising ethyl acetate. In one embodiment, the third residue in line 252 is withdrawn from third column 251 at a temperature higher than the operating temperature of the second column 241. Preferably, the third residue in line 252 is integrated to heat one or more other streams or is reboiled prior to be returned to the second column 241.

Although the third residue may be directly recycled to second column 241, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

In addition, in some embodiments, a portion of the third residue may be directed to the PRS unit 150 of the carbonylation process 100 to extract the derivative stream 163 via line 255.

Third column 251 is preferably a tray column. In one embodiment, third column 251 may operate at a pressure from 0.1 kPa to 510 kPa, e.g., from 1 kPa to 475 kPa or from 1 kPa to 375 kPa. At atmospheric pressure, the temperature of the third distillate exiting in line 253 preferably is from 60° C. to 110° C., e.g., from 70° C. to 100° C. or from 75° C. to 95° C. The temperature of the third residue in line 252 preferably is from 70° C. to 115° C., e.g., from 80° C. to 110° C. or from 85° C. to 105° C.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system. Preferably at least one side stream is used to remove impurities from the third column 251. The impurities may be purged and/or retained within the system. The composition of the ethanol product obtained from the third distillate in FIG. 2 is shown below in Table 6.

The third distillate in line 253 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 241, the second distillate preferably is refluxed as shown in FIG. 2, at a reflux ratio of 1:10 to 10:1, e.g., from 1:5 to 5:1 or from 1:3 to 3:1. The second distillate in line 243 may be purged or recycled to the reaction zone 210. The second distillate in line 243 may be further processed in an optional fourth column 261, also referred to as the "acetaldehyde removal column." In optional fourth column 261, the second distillate is separated into a fourth distillate, which comprises acetaldehyde, in line 263 and a fourth residue, which comprises ethyl acetate, in line 262. The fourth distillate preferably is refluxed at a reflux ratio of from 1:20 to 20:1, e.g., from 1:15 to 15:1 or from 1:10 to 10:1, and a portion of the fourth distillate is returned to the reaction zone 210. For example, the fourth distillate may be combined with the acetic acid feed, added to the vaporizer 201, or added directly to the reactor 211. The fourth distillate preferably is co-fed with the acetic acid in feed line 205. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of optional fourth column 261 may be purged via line 262. The fourth residue primarily comprises ethyl acetate and ethanol, which may be suitable for use as a solvent mixture or in the production of esters. In one preferred embodiment, the acetaldehyde is removed from the second distillate in fourth column 261 such that no detectable amount of acetaldehyde is present in the residue of column 261.

Optional fourth column 261 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 261 may operate at a pressure that is higher than the pressure of the other columns.

The temperature of the fourth distillate exiting in line 263 preferably is from 60° C. to 110° C., e.g., from 70° C. to 100° C. or from 75° C. to 95° C. The temperature of the residue in line 262 preferably is from 70° C. to 115° C., e.g., from 80° C. to 110° C. or from 85° C. to 110° C.

In one embodiment, a portion of the third residue is recycled in line 244 to second column 241. In one embodiment, recycling the third residue further reduces the aldehyde components in the second residue and concentrates these aldehyde components in second distillate in line 243 and is thereby sent to the fourth column 261, wherein the aldehydes may be more easily separated. The third distillate, e.g. intermediate stream, in line 253 may have lower concentrations of aldehydes and esters due to the recycling of third residue.

Although the composition of the third residue may vary depending on the specific separation conditions, in preferred embodiments the third residue comprises water and may be referred to herein as a water stream. Exemplary compositions for the third distillate and third residue (water stream) are provided below in Table 4. It should also be understood that the distillate may also contain other components, not listed, such as components in the feed.

TABLE 4

THIRD COLUMN 251

|  | Conc. (wt. %) | Conc. (wt. %) | Conc. (wt. %) |
| --- | --- | --- | --- |
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 97 to 100 | 98 to 100 | 99 to 100 |
| Ethanol | <0.005 | <0.002 | <0.001 |
| Ethyl Acetate | <0.001 | <0.0005 | not detectable |
| Acetic Acid | <0.5 | <0.1 | <0.05 |
| Organic Impurities | <0.001 | <0.0005 | not detectable |

Optionally a portion of the third residue stream is directed to the carbonylation system 100 to serve as an extraction medium.

FIG. 5 illustrates another exemplary separation system that has a similar reaction zone 210 as FIGS. 2-4 and produces a liquid stream 222, e.g., crude ethanol mixture, for further separation. In one preferred embodiment, the reaction zone 210 of FIG. 5 operates at above 70% acetic acid conversion, e.g., above 85% conversion or above 90% conversion. Thus, the acetic acid concentration in the liquid stream 222 may be low. Derivative stream 163 and acetic acid feed 132 are also fed to the reaction zone 210 in a similar manner as FIGS. 2-4.

Liquid stream 222 is fed to the first column 271 to yield a first distillate 273 and first residue 272. Liquid stream 222 may be introduced in the middle or lower portion of first column 271, also referred to as acid-water column. In one embodiment, no entrainers are added to first column 271. Water and acetic acid, along with any other heavy components, if present, are removed from liquid stream 222 and are withdrawn, preferably continuously, as a first residue in line 272. Preferably, a substantial portion of the water in the crude ethanol mixture that is fed to first column 271 may be removed in the first residue, for example, up to about 75% or to about 90% of the water from the crude ethanol mixture. In one embodiment, 30 to 90% of the water in the crude ethanol mixture is removed in the residue, e.g., from 40 to 88% of the water or from 50 to 84% of the water.

When first column 271 is operated under about 170 kPa, the temperature of the residue exiting in line 272 preferably is from 90° C. to 130° C., e.g., from 95° C. to 120° C. or from 100° C. to 115° C. The temperature of the distillate exiting in line 273 preferably is from 60° C. to 90° C., e.g., from 65° C. to 85° C. or from 70° C. to 80° C. In some embodiments, the pressure of first column 271 may also range from 0.1 kPa to 510 kPa, e.g., from 1 kPa to 475 kPa or from 1 kPa to 375 kPa.

The first distillate in line 273 comprises some water in addition to ethanol and other organics. In terms of ranges, the water concentration in the first distillate in line 273 preferably is from 4 wt. % to 38 wt. %, e.g., from 7 wt. % to 32 wt. %, or from 7 to 25 wt. %. A portion of first distillate in line 275 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 271. The condensed portion of the first distillate may also be fed to a second column 291.

As shown, the remaining portion of the first distillate in line 274 is fed to a water separation unit 281. Water separation unit 281 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 281 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise from two to five beds. Water separator 281 may remove at least 95% of the water from the portion of first distillate in line 273, and more preferably from 99% to 99.99% of the water from the first distillate, in a water stream 282. All or a portion of water stream 282 may be returned to first column 271 in line 284, where the water preferably is ultimately recovered from column 271 in the first residue in line 272. Additionally or alternatively, all or a portion of water stream 282 may be removed from the hydrogenation system via line 285. The remaining portion of first distillate exits the water separator 281 as ethanol mixture stream 283. Ethanol mixture stream 283 may have a low water concentration of less than 10 wt. %, e.g., less than 6 wt. % or less than 2 wt. %.

In one optional embodiment, all or a portion of either or both the first residue in line 272 and/or the separated stream in line 285 may be directed to the carbonylation system, e.g., as shown in FIG. 3, to serve as an extraction medium. In a preferred embodiment, all or a portion of the first residue and/or line 285 is directed to the PRS 150 of the carbonylation system to serve as an extractant (e.g., stream 184 in FIG. 3) for extracting acetaldehyde from a mixture comprising methyl iodide and acetaldehyde.

Preferably, ethanol mixture stream 283 is not returned or refluxed to first column 271. The condensed portion of the first distillate in line 275 may be combined with ethanol mixture stream 283 to control the water concentration fed to the second column 291. For example, in some embodiments the first distillate may be split into equal portions, while in other embodiments, all of the first distillate may be condensed or all of the first distillate may be processed in the water separation unit. In FIG. 5, the condensed portion in line 275 and ethanol mixture stream 283 are co-fed to second column 291. In other embodiments, the condensed portion in line 275 and ethanol mixture stream 283 may be separately fed to second column 291. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 291 in FIG. 5, also referred to as the "light ends column," removes ethyl acetate and acetaldehyde from the first distillate in line 275 and/or ethanol mixture stream 283. Ethyl acetate and acetaldehyde are removed as a second distillate in line 293 and ethanol is removed as the second residue in line 292. Preferably ethanol is recovered with low amounts of ethyl acetate, acetaldehyde, and/or acetal, e.g., less than 1 wt. % or more preferably less than 0.5 wt. %. The ethanol product obtained from second residue in FIG. 5, is shown below in Table 5. Preferably, the ethanol product comprises less than 1 wt. % diethyl acetal, e.g., less than 0.5 wt. % or less than 0.01 wt. %.

Second column 291 may be a tray column or packed column. In one embodiment, second column 291 is a tray column having from 5 to 120 trays, e.g., from 15 to 100 trays or from 20 to 90 trays. In one embodiment, second column 291 may operate at a pressure ranging from 0.1 kPa to 510 kPa, e.g., from 10 kPa to 450 kPa or from 50 kPa to 350 kPa. Although the temperature of second column 291 may vary, when at about 20 kPa to 70 kPa, the temperature of the second residue exiting in line 292 preferably is from 30° C. to 75° C., e.g., from 35° C. to 70° C. or from 40° C. to 65° C. The temperature of the second distillate exiting in line 293 preferably is from 20° C. to 55° C., e.g., from 25° C. to 50° C. or from 30° C. to 45° C.

The total concentration of water fed to second column 291 preferably is less than 10 wt. %, as discussed above. When first distillate in line 275 and/or ethanol mixture stream 283 comprises minor amounts of water, e.g., less than 1 wt. % or less than 0.5 wt. %, additional water may be fed to the second column 291 as an extractive agent in the upper portion of the column. A sufficient amount of water is preferably added via the extractive agent such that the total concentration of water fed to second column 291 is from 1 to 10 wt. % water, e.g., from 2 to 6 wt. %, based on the total weight of all components fed to second column 291. If the extractive agent comprises water, the water may be obtained from an external source or from an internal return/recycle line from one or more of the other columns or water separators.

Suitable extractive agents may also include, for example, dimethylsulfoxide; glycerine; diethylene glycol; 1-naphthol; hydroquinone; N,N'-dimethylformamide; 1,4-butanediol; ethylene glycol-1,5-pentanediol; propylene glycol-tetraethylene glycol-polyethylene glycol; glycerine-propylene glycol-tetraethylene glycol-1,4-butanediol; ethyl ether; methyl formate; cyclohexane; N,N'-dimethyl-1,3-propanediamine; N,N'-dimethylethylenediamine; diethylene triamine; hexamethylene diamine; 1,3-diaminopentane; an alkylated thiopene; dodecane; tridecane; tetradecane; chlorinated paraffins; or a combination thereof. When extractive agents are used, a suitable recovery system, such as a further distillation column, may be used to recycle the extractive agent.

The second distillate in line 293, which comprises ethyl acetate and/or acetaldehyde, preferably is refluxed as shown in FIG. 5, for example, at a reflux ratio of from 1:30 to 30:1, e.g., from 1:10 to 10:1 or from 1:3 to 3:1. In one aspect, not shown, the second distillate 293 or a portion thereof may be returned to reactor 211.

In one embodiment, the second distillate in line 293 and/or a refined second distillate, or a portion of either or both streams, may be further separated to produce an acetaldehyde-containing stream and an ethyl acetate-containing stream. For example, the optional fourth column 261 of FIGS. 2-4 may be used to separate second distillate in line 293. This may allow a portion of either the resulting acetaldehyde-containing stream or ethyl acetate-containing stream to be recycled to reactor 211 while purging the other stream. The purge stream may be valuable as a source of either ethyl acetate and/or acetaldehyde. In one embodiment, it may be preferred to operate second column 291 in FIG. 5 at a pressure less than atmospheric pressure to decrease the energy required to separate ethyl acetate and ethanol.

Another exemplary two column separation scheme is shown in FIG. 6. Derivative stream 163 and acetic acid feed 132 are also fed to the reaction zone 210 in a similar manner as FIGS. 2-4. In this embodiment, liquid stream 222 is introduced in the upper part of first column 301, e.g., upper half or upper third. In one embodiment, no entrainers are added to first column 301. In first column 301, a weight majority of the ethanol, water, acetic acid, and other heavy components, if present, are removed from liquid stream 222 and are withdrawn, preferably continuously, as the first residue in line 302. First column 301 also forms an overhead distillate, which is withdrawn in line 303, and which may be condensed and refluxed, for example, at a ratio of from 30:1 to 1:30, e.g., from 10:1 to 1:10 or from 1:5 to 5:1. The first distillate in line 303 preferably comprises a weight majority of the ethyl acetate from liquid line 222. In addition, distillate in line 303 may also comprise acetaldehyde.

When column 301 is operated under about 170 kPa, the temperature of the residue exiting in line 302 preferably is from 70° C. to 155° C., e.g., from 90° C. to 130° C. or from 100° C. to 110° C. The base of column 301 may be maintained at a relatively low temperature by withdrawing a residue stream comprising ethanol, water, and acetic acid, thereby providing an energy efficiency advantage. The temperature, at 170 kPa, of the distillate exiting in line 303 preferably is from 75° C. to 100° C., e.g., from 75° C. to 83° C. or from 81° C. to 84° C.

In one embodiment, column 301 of FIG. 6 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 302 to water in the distillate in line 303 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 211. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to reactor 211. In some embodiments, the distillate may be further separated, e.g., in the optional fourth column 261 of FIGS. 2-4, into an acetaldehyde stream and an ethyl acetate stream. Either of these streams may be returned to the reactor 211 or separated from system as a separate product.

To recover ethanol, the residue in line 302 may be further separated in a second column 311, also referred to as an "acid separation column." An acid separation column may be used when the acetic acid concentration in the first residue is greater than 1 wt. %, e.g., greater than 5 wt. %. The first residue in line 302 is introduced to second column 311 preferably in the top part of column 311, e.g., top half or top third. Second column 311 yields a second residue in line 312 comprising acetic acid and water, and a second distillate in line 313 comprising ethanol.

Second column 311 may be a tray column or packed column. In one embodiment, second column 311 is a tray column having from 5 to 150 trays, e.g., from 15 to 50 trays or from 20 to 45 trays. In some embodiments, the second column 311 of FIG. 6 is operated at a pressure ranging from 0.1 kPa to 510 kPa, e.g., from 1 kPa to 475 kPa or from 1 kPa to 375 kPa.

In the system shown in FIG. 6, it is preferred to operate the first column 301 at an increased pressure, because second column 311 comprises very low amounts of acetaldehyde and/or acetals. Generally, the pressure of second column 311 may range from 0.1 kPa to 510 kPa, e.g., from 1 kPa to 475 kPa or from 1 kPa to 375 kPa. At atmospheric pressure the temperature of the second residue exiting in line 312 preferably is from 95° C. to 130° C., e.g., from 100° C. to 125° C. or from 110° C. to 120° C. The temperature of the second distillate exiting in line 313 preferably is from 60° C. to 105° C., e.g., from 75° C. to 100° C. or from 80° C. to 100° C.

The weight ratio of ethanol in the second distillate in line 313 to ethanol in the second residue in line 312 preferably is at least 35:1. In one embodiment, the weight ratio of water in the second residue 312 to water in the second distillate 313 is greater than 2:1, e.g., greater than 4:1 or greater than 6:1. In addition, the weight ratio of acetic acid in the second residue 312 to acetic acid in the second distillate 313 preferably is greater than 10:1, e.g., greater than 15:1 or greater than 20:1. Preferably, the second distillate in line 313 is substantially free of acetic acid and may only contain, if any, trace amounts of acetic acid. Preferably, the second distillate in line 313 contains substantially no ethyl acetate.

The remaining water from the second distillate in line 313 may be removed in further embodiments of the present invention. Depending on the water concentration, the ethanol product may be derived from the second distillate in line 313. Some applications, such as industrial ethanol applications, may tolerate water in the ethanol product, while other applications, such as fuel applications, may require an anhydrous ethanol. The amount of water in the distillate of line 313 may be closer to the azeotropic amount of water, e.g., at least 4 wt. %, preferably less than 20 wt. %, e.g., less than 12 wt. % or less than 7.5 wt. %. Water may be removed from the second distillate in line 313 using several different separation techniques as described herein. Particularly preferred techniques include the use of distillation column, membranes, adsorption units, and combinations thereof.

Optionally, all or a portion of the second residue 312 is directed to a carbonylation system, e.g., as shown in FIGS. 2-4, to serve as an extraction medium. In a preferred embodiment, all or a portion of the second residue 312 is directed to the PRS 150 of the carbonylation system to serve as an extractant 164 for extracting acetaldehyde from a mixture comprising methyl iodide and acetaldehyde.

In one embodiment, any of the residue streams from the hydrogenation section 200 may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor. The resulting water stream may be directed to a carbonylation system for use as an extractant as discussed above.

In other embodiments, for example, where the second residue comprises less than 50 wt. % acetic acid, possible options include one or more of: (i) neutralizing the acetic acid, or (ii) reacting the acetic acid with an alcohol. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

The columns shown in figures may comprise any distillation column capable of performing the desired separation and/or purification. For example, other than the acid columns describe above, the other columns preferably are a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from a stream that primarily comprises ethanol from exemplary systems shown in the figures. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 75 to 99.9 | 80 to 99.5 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Diethyl Acetal | <1 | 0.0001 to 0.1 | 0.0001 to 0.01 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, examples are provided below. It should be understood that these examples are for illustrative purposes only and are not to be construed as limiting the invention in any manner.

EXAMPLES

Example 1

1 mL of starting stream comprising methyl iodide and acetaldehyde was contacted with 1 mL of the corresponding extractant at 25° C. The mixture was shaken five times and left for five minutes. The two phases were then separated and the resulting concentrations were determined by gas chromatography. This was conducted for three different concentrations, as shown below in Table 6.

TABLE 6

| | | Extractor 180 | | | | | |
|---|---|---|---|---|---|---|---|
| | | Conc. 1 (wt %) | | Conc. 2 (wt %) | | Conc. 3 (wt %) | |
| | Extractant | AcH | MeI | AcH | MeI | AcH | MeI |
| Starting Stream 177 | | 12.41 | 0.88 | 24.62 | 1.24 | 28.41 | 1.81 |
| Resulting Stream 183 | Pentane | 11.22 | 0.06 | 22.00 | 0.06 | 24.53 | 0.07 |
| | Hexane | 11.47 | 0.11 | 22.20 | 0.07 | 25.51 | 0.16 |
| | Octane | 11.20 | 0.07 | 23.27 | 0.09 | 26.80 | 0.09 |
| | Nonane | 11.85 | 0.13 | 22.77 | 0.05 | 25.73 | 0.08 |
| | Decane | 11.71 | 0.13 | 22.81 | 0.06 | 26.75 | 0.08 |
| | Dodecane | 11.90 | 0.08 | 22.20 | 0.05 | 26.02 | 0.08 |
| | Kerosene | 11.81 | 0.06 | 22.51 | 0.05 | 25.60 | 0.08 |

Example 2

The same procedure was followed as in Example 1, using concentration 3 from Table 6 above. The procedure was performed for three different ratios. As is shown in Table 7 below, Ratio 1 is 0.5 mL extractant contacted with 1 mL of starting stream comprising methyl iodide and acetaldehyde. Ratio 2 is 1 mL extractant contacted with 1 mL starting stream comprising methyl iodide and acetaldehyde. Ratio 3 is 3 mL extractant contacted with 1 mL of starting stream comprising methyl iodide and acetaldehyde.

TABLE 7

| | | Extractor 180 | | | | | |
|---|---|---|---|---|---|---|---|
| | | Conc. (wt %) | | Conc. (wt %) | | Conc. (wt %) | |
| | | AcH | MeI | AcH | MeI | AcH | MeI |
| Starting Stream 177 | | 28.41 | 1.81 | 28.41 | 1.81 | 28.41 | 1.81 |
| | | Extractant: Starting Stream Ratio | | | | | |
| | Extractant | Ratio 1 (0.5:1) | | Ratio 2 (1:1) | | Ratio 3 (3:1) | |
| Resulting Stream 183 | Pentane | 26.82 | 0.12 | 24.53 | 0.07 | 21.52 | nd |
| | Hexane | 25.93 | 0.14 | 25.51 | 0.16 | 23.74 | nd |
| | Octane | 26.10 | 0.10 | 26.80 | 0.09 | 24.02 | nd |
| | Nonane | 25.60 | 0.08 | 25.73 | 0.08 | 24.09 | nd |
| | Decane | 25.34 | 0.09 | 26.75 | 0.08 | 24.09 | nd |
| | Dodecane | 25.73 | 0.13 | 26.02 | 0.08 | 24.36 | nd |
| | Kerosene | 26.42 | 0.10 | 25.60 | 0.08 | 24.42 | nd |

While the invention has been described in detail, modifications within the spirit and scope of the invention will be readily apparent to those of skill in the art. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, the process comprising the steps of:
reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst;
extracting at least a portion of the reaction solution or a derivative thereof with at least one hydrophobic extractant to obtain an acetic acid intermediate that is substantially free of methyl iodide;
introducing the acetic acid intermediate into a second reactor in the presence of a second catalyst to form a crude ethanol product; and
recovering ethanol from the crude ethanol product.

2. The process of claim 1, wherein the acetic acid intermediate comprises less than 10 wppm methyl iodide.

3. The process of claim 1, wherein the acetic acid intermediate comprises less than 10 wppm of alkyl halides.

4. The process of claim 1, wherein the at least one hydrophobic extractant comprises a $C_5$ to $C_{16}$ alkane.

5. The process of claim 1, wherein the at least one hydrophobic extractant comprises a $C_8$ to $C_{12}$ alkane.

6. The process of claim 1, wherein the at least one hydrophobic extractant comprises decane, dodecane, or combinations thereof.

7. The process of claim 1, wherein the at least one hydrophobic extractant comprises dodecane.

8. The process of claim 1, wherein the extraction step is a multi-stage extraction.

9. The process of claim 1, wherein a raffinate is obtained during the extraction step and wherein at least a portion of the raffinate is introduced into the first reactor.

10. The process of claim 1, wherein the acetic acid intermediate is substantially free of methanol, methyl acetate, methyl formate, and/or dimethyl ether.

11. The process of claim 1, wherein the acetic acid intermediate comprises less than 0.01 wt. % of methanol, methyl acetate, methyl formate, and/or dimethyl ether.

12. The process of claim 1, further comprising:
flashing the reaction solution to obtain a vapor stream; and wherein the vapor stream is extracted with the hydrophobic extractant to obtain the acetic acid intermediate.

13. The process of claim 1, further comprising:
flashing the reaction solution to obtain a vapor stream;
separating the vapor stream in a light ends column to yield an acetic acid sidestream and an overhead comprising one or more permanganate reducing compounds, methyl acetate, methanol, water, and methyl iodide; and
and wherein the acetic acid sidestream is extracted with the hydrophobic extractant to obtain the acetic acid intermediate.

14. The process of claim 13, wherein the permanganate reducing compounds are selected from the group consisting of acetaldehyde, acetone, methyl ethyl ketone, butyraldehyde, crotonaldehyde, 2-ethyl crotonaldehyde, 2-ethyl butyraldehyde, the aldol condensation products thereof, and mixtures thereof.

15. The process of claim 1, wherein the crude ethanol product is substantially free of methyl iodide.

16. The process of claim 1, wherein the crude ethanol product comprises less than 10 wppm of methyl iodide.

17. The process of claim 1, wherein the first catalyst is different than the second catalyst.

18. The process of claim 1, wherein the acetic acid intermediate further comprises water in an amount from 0.15 to 25 wt. %.

19. The process of claim 1, further comprising:
flashing the reaction solution to obtain a vapor stream;
separating the vapor stream in a light ends column to yield an acetic acid sidestream and an overhead comprising one or more permanganate reducing compounds, methyl acetate, methanol, water, and methyl iodide;
biphasically separating the overhead stream into an aqueous stream; and
extracting a portion of the aqueous stream with at least one hydrophobic extractant to obtain an aldehyde-enriched stream.

20. The process of claim 19, further comprising:
introducing the aldehyde-enriched stream into the second reactor in the presence of the second catalyst to produce ethanol, wherein the aldehyde-enriched stream is substantially free of methyl iodide.

21. A process for producing ethanol, the process comprising the steps of:
reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst;

flashing the reaction solution to obtain a vapor stream;

extracting a condensed portion of the vapor stream with at least one hydrophobic extractant to obtain an acetic acid intermediate that is substantially free of methyl iodide;

introducing the acetic acid intermediate into a second reactor in the presence of a second catalyst to form a crude ethanol product; and recovering ethanol from the crude ethanol product.

22. A process for producing ethanol, the process comprising the steps of:

reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a first catalyst;

flashing the reaction solution to obtain a vapor stream;

separating the vapor stream in a light ends column to yield an acetic acid sidestream and an overhead comprising one or more permanganate reducing compounds, methyl acetate, methanol, water, and methyl iodide, wherein the permanganate reducing compounds are selected from the group consisting of acetaldehyde, acetone, methyl ethyl ketone, butyraldehyde, crotonaldehyde, 2-ethyl crotonaldehyde, 2-ethyl butyraldehyde, the aldol condensation products thereof, and mixtures thereof;

extracting a portion of the acetic acid sidestream with at least one hydrophobic extractant to obtain an acetic acid intermediate that is substantially free of methyl iodide;

introducing the acetic acid intermediate into a second reactor in the presence of a second catalyst to form a crude ethanol product; and recovering ethanol from the crude ethanol product.

* * * * *